US008980290B2

(12) United States Patent  
Carrara et al.

(10) Patent No.: US 8,980,290 B2
(45) Date of Patent: Mar. 17, 2015

(54) TRANSDERMAL COMPOSITIONS FOR ANTICHOLINERGIC AGENTS

(75) Inventors: Dario Norberto R. Carrara, Oberwil (CH); Arnaud Grenier, Steinbrunn le haut (FR)

(73) Assignee: Antares Pharma IPL AG, Zug (CH)

( * ) Notice: Subject to any disclaimer, the term of this patent is extended or adjusted under 35 U.S.C. 154(b) by 374 days.

(21) Appl. No.: 12/614,216

(22) Filed: Nov. 6, 2009

(65) Prior Publication Data

US 2010/0216880 A1 Aug. 26, 2010

Related U.S. Application Data

(63) Continuation-in-part of application No. 11/755,923, filed on May 31, 2007, which is a continuation-in-part of application No. 11/371,042, filed on Mar. 7, 2006, now Pat. No. 7,335,379, which is a continuation of application No. PCT/EP2004/011175, filed on Oct. 6, 2004, which is a continuation-in-part of application No. 10/798,111, filed on Mar. 10, 2004, said application No. 11/755,923 is a continuation-in-part of application No. 11/634,005, filed on Dec. 4, 2006, now Pat. No. 7,404,965, which is a continuation of application No. 10/343,570, filed as application No. PCT/EP01/09007 on Aug. 3, 2001, now Pat. No. 7,214,381.

(60) Provisional application No. 60/510,613, filed on Oct. 10, 2003, provisional application No. 60/453,604, filed on Mar. 11, 2003.

(30) Foreign Application Priority Data

Aug. 3, 2000 (WO) .................. PCT/EP00/07533

(51) Int. Cl.
*A61K 9/00* (2006.01)
*A61K 31/216* (2006.01)
*A61K 47/00* (2006.01)
*A61K 9/06* (2006.01)
*A61K 31/56* (2006.01)
*A61K 47/10* (2006.01)
*A61K 47/32* (2006.01)
*A61K 47/38* (2006.01)

(52) U.S. Cl.
CPC ................ *A61K 9/06* (2013.01); *A61K 9/0014* (2013.01); *A61K 31/216* (2013.01); *A61K 31/56* (2013.01); *A61K 47/10* (2013.01); *A61K 47/32* (2013.01); *A61K 47/38* (2013.01)
USPC ........................... 424/400; 514/534; 514/772

(58) Field of Classification Search
CPC ..... A61K 9/0014; A61K 9/06; A61K 31/216; A61K 47/10; A61K 47/32
USPC .................. 424/400; 514/534, 772
See application file for complete search history.

(56) References Cited

U.S. PATENT DOCUMENTS

| 1,979,385 | A | 11/1934 | Harvey | |
|---|---|---|---|---|
| 2,990,332 | A | 6/1961 | Keating | 167/65 |
| 3,143,465 | A | 8/1964 | Keating | 167/65 |
| 3,650,280 | A | 3/1972 | Roberts et al. | |
| 3,891,696 | A | 6/1975 | Bodor et al. | 560/142 |
| 3,989,816 | A | 11/1976 | Rajadhyaksha | 424/60 |
| 4,082,881 | A | 4/1978 | Chen et al. | 514/39 |
| 4,221,778 | A | 9/1980 | Raghunathan | 424/31 |
| 4,315,925 | A | 2/1982 | Hussain et al. | 514/177 |
| 4,316,893 | A | 2/1982 | Rajadhyaksha | 424/180 |
| 4,383,993 | A | 5/1983 | Hussain et al. | 514/177 |
| 4,390,532 | A | 6/1983 | Stuttgen et al. | 514/56 |
| 4,405,616 | A | 9/1983 | Rajadhyaksha | 424/60 |
| 4,537,776 | A | 8/1985 | Cooper | 514/424 |
| 4,557,934 | A | 12/1985 | Cooper | 424/128 |
| 4,568,343 | A | 2/1986 | Leeper et al. | 604/896 |
| 4,597,961 | A | 7/1986 | Etscorn | 424/448 |
| 4,704,406 | A | 11/1987 | Stanislaus et al. | 514/570 |
| 4,764,381 | A | 8/1988 | Bodor et al. | 424/449 |
| 4,783,450 | A | 11/1988 | Fawzi et al. | 514/78 |
| 4,808,411 | A | 2/1989 | Lu et al. | 424/441 |

(Continued)

FOREIGN PATENT DOCUMENTS

| EP | 0 249 397 A2 | 12/1987 |
|---|---|---|
| EP | 0 250 125 B1 | 12/1987 |
| EP | 0 261 429 A1 | 3/1988 |
| EP | 0 267 617 A1 | 5/1988 |
| EP | 0 271 983 A1 | 6/1988 |
| EP | 0 279 977 A2 | 8/1988 |
| EP | 0 325 613 B1 | 6/1989 |
| EP | 0 367 431 A1 | 5/1990 |
| EP | 0 409 383 B1 | 1/1991 |
| EP | 0 435 200 B1 | 7/1991 |

(Continued)

OTHER PUBLICATIONS

Donald A. Godwin, Mark R. Player, J. Walter Sowell and Bozena B. Michniak, "Synthesis and investigation of urea compounds as transdermal penetration enhancers", International Journal of Pharmaceutics, 167 (1998) 165-175.*

(Continued)

*Primary Examiner* — John Pak
*Assistant Examiner* — Nathan W Schlientz
(74) *Attorney, Agent, or Firm* — Winston & Strawn LLP

(57) ABSTRACT

The present invention relates generally to compositions or formulations for transdermal or transmucosal administration of anticholinergic agents such as oxybutynin. The invention utilizes a novel delivery vehicle and is a substantially malodorous-free and irritation free transdermal formulation which is substantially free of long chain fatty alcohols, long-chain fatty acids, and long-chain fatty esters. A method is disclosed for treating a subject for urinary incontinence with these formulations while reducing the incidences of peak concentrations of drug and undesirable side effects associated with oral anticholinergics.

20 Claims, 14 Drawing Sheets

(56) References Cited

U.S. PATENT DOCUMENTS

| | | | |
|---|---|---|---|
| 4,832,953 A | 5/1989 | Campbell et al. | 424/448 |
| 4,863,970 A | 9/1989 | Patel et al. | 514/784 |
| 4,883,660 A | 11/1989 | Blackman et al. | 424/78 |
| 4,952,560 A | 8/1990 | Kigasawa et al. | 514/2 |
| 4,956,171 A | 9/1990 | Chang | 424/449 |
| 4,973,468 A | 11/1990 | Chiang et al. | 424/449 |
| 5,041,439 A | 8/1991 | Kasting et al. | 514/227.2 |
| 5,053,227 A | 10/1991 | Chiang et al. | 424/448 |
| 5,059,426 A | 10/1991 | Chiang et al. | 424/449 |
| 5,064,654 A | 11/1991 | Berner et al. | 424/448 |
| 5,071,657 A | 12/1991 | Oloff et al. | 424/486 |
| 5,112,842 A | 5/1992 | Zierenberg et al. | 514/367 |
| 5,128,138 A | 7/1992 | Blank | 424/449 |
| 5,134,127 A | 7/1992 | Stella et al. | 514/58 |
| 5,164,190 A | 11/1992 | Patel et al. | 424/448 |
| 5,175,190 A | 12/1992 | Burton et al. | 514/560 |
| 5,178,879 A | 1/1993 | Adekunle et al. | 424/484 |
| 5,188,825 A | 2/1993 | Hes et al. | 424/78.1 |
| 5,225,189 A | 7/1993 | Pena | 424/70 |
| 5,230,896 A | 7/1993 | Yeh et al. | 424/443 |
| 5,232,703 A | 8/1993 | Blank | 424/449 |
| 5,238,933 A | 8/1993 | Catz et al. | 514/236.2 |
| 5,278,176 A | 1/1994 | Lin | 514/343 |
| 5,352,457 A | 10/1994 | Jenkins | 424/448 |
| 5,371,005 A | 12/1994 | Fujishiro et al. | 435/190 |
| 5,374,421 A | 12/1994 | Tashiro et al. | 424/70.12 |
| 5,376,645 A | 12/1994 | Stella et al. | 514/58 |
| 5,380,763 A | 1/1995 | Sato et al. | 514/724 |
| 5,397,771 A | 3/1995 | Bechgaard et al. | 514/2 |
| 5,453,279 A | 9/1995 | Lee et al. | 424/448 |
| 5,527,832 A | 6/1996 | Chi et al. | 514/772.4 |
| 5,532,278 A | 7/1996 | Aberg et al. | 514/617 |
| 5,549,888 A | 8/1996 | Venkateswaran | 424/78.02 |
| 5,552,153 A | 9/1996 | Behl | 424/449 |
| 5,576,279 A | 11/1996 | Pyles | 510/122 |
| 5,580,574 A | 12/1996 | Behl et al. | 424/449 |
| 5,601,839 A | 2/1997 | Quan et al. | 424/448 |
| 5,602,017 A | 2/1997 | Fujishiro et al. | 435/190 |
| 5,603,947 A | 2/1997 | Wong et al. | 424/448 |
| 5,629,021 A | 5/1997 | Wright | 424/489 |
| 5,633,008 A | 5/1997 | Osborne et al. | 424/449 |
| 5,658,587 A | 8/1997 | Santus et al. | 424/448 |
| 5,660,839 A | 8/1997 | Allec et al. | 424/401 |
| 5,662,890 A | 9/1997 | Punto et al. | 424/59 |
| 5,665,560 A | 9/1997 | Fujishiro et al. | 435/11 |
| 5,677,346 A | 10/1997 | Aberg et al. | 51/617 |
| 5,716,638 A | 2/1998 | Touitou | 424/450 |
| 5,719,197 A | 2/1998 | Kanios et al. | 514/772.6 |
| 5,731,303 A | 3/1998 | Hsieh | 514/183 |
| 5,736,577 A | 4/1998 | Aberg et al. | 514/617 |
| 5,783,207 A | 7/1998 | Stanley et al. | 424/440 |
| 5,785,991 A | 7/1998 | Burkoth et al. | 424/448 |
| 5,786,357 A | 7/1998 | Young et al. | 514/249 |
| 5,798,242 A | 8/1998 | Fujishiro et al. | 435/190 |
| 5,814,659 A | 9/1998 | Elden | 514/452 |
| 5,831,035 A | 11/1998 | Timms | 530/389.1 |
| 5,834,010 A | 11/1998 | Quan et al. | 424/448 |
| 5,843,482 A | 12/1998 | Rhodes et al. | 424/653 |
| 5,846,983 A | 12/1998 | Sandborn et al. | 514/343 |
| 5,855,905 A | 1/1999 | Oettel et al. | 424/426 |
| 5,855,920 A | 1/1999 | Chein | 424/568 |
| 5,891,462 A | 4/1999 | Carrara | 424/449 |
| 5,900,250 A | 5/1999 | Lee et al. | 424/448 |
| 5,904,931 A | 5/1999 | Lipp et al. | 424/449 |
| 5,922,349 A | 7/1999 | Elliesen et al. | 424/449 |
| 5,925,372 A | 7/1999 | Berner et al. | 424/448 |
| 5,932,243 A | 8/1999 | Fricker et al. | 424/450 |
| 5,935,604 A | 8/1999 | Illum | 424/501 |
| 5,945,405 A | 8/1999 | Spanton et al. | 514/29 |
| 5,955,455 A | 9/1999 | Labrie | 514/179 |
| 5,968,919 A | 10/1999 | Samour et al. | 514/177 |
| 6,008,192 A | 12/1999 | Al-Razzak et al. | 514/11 |
| 6,034,079 A | 3/2000 | Sandberg et al. | 514/225.8 |
| 6,060,077 A | 5/2000 | Meignant | 424/434 |
| 6,071,959 A | 6/2000 | Rhodes et al. | 514/535 |
| 6,093,722 A | 7/2000 | Kojima et al. | |
| 6,096,733 A | 8/2000 | Lubkin | 514/182 |
| 6,123,961 A | 9/2000 | Aberg | 424/468 |
| 6,124,355 A | 9/2000 | Guittard et al. | 517/534 |
| 6,133,248 A | 10/2000 | Stella | 514/58 |
| 6,153,216 A | 11/2000 | Cordes et al. | 424/449 |
| 6,165,497 A | 12/2000 | Osborne et al. | 424/449 |
| 6,166,044 A | 12/2000 | Sandborn et al. | 514/343 |
| 6,180,803 B1 | 1/2001 | Piasco et al. | 552/510 |
| 6,238,689 B1 | 5/2001 | Rhodes et al. | 424/436 |
| 6,267,985 B1 | 7/2001 | Chen et al. | 424/451 |
| 6,284,234 B1 | 9/2001 | Niemiec et al. | 424/78.07 |
| 6,299,900 B1 | 10/2001 | Reed et al. | 424/449 |
| 6,309,843 B1 | 10/2001 | Timms | 435/7.1 |
| 6,319,913 B1 | 11/2001 | Mak et al. | 514/179 |
| 6,383,471 B1 | 5/2002 | Chen et al. | 424/45 |
| 6,417,205 B1 | 7/2002 | Cooke et al. | 514/343 |
| 6,426,078 B1 | 7/2002 | Bauer et al. | 424/401 |
| 6,432,446 B2 | 8/2002 | Aberg | 424/468 |
| 6,440,454 B1 | 8/2002 | Santoro et al. | 424/449 |
| 6,444,234 B1 | 9/2002 | Kirby et al. | 424/725 |
| 6,451,300 B1 | 9/2002 | Dunlop et al. | 424/70.27 |
| 6,465,005 B1 | 10/2002 | Biali et al. | 424/449 |
| 6,476,012 B2 | 11/2002 | Hochberg | 514/182 |
| 6,479,076 B2 | 11/2002 | Blank | 424/484 |
| 6,497,897 B2 | 12/2002 | Hidaka et al. | 424/449 |
| 6,503,894 B1 | 1/2003 | Dudley et al. | 514/178 |
| 6,545,046 B2 | 4/2003 | Sherratt et al. | 514/534 |
| 6,579,865 B2 | 6/2003 | Mak et al. | 514/179 |
| 6,586,000 B2 | 7/2003 | Luo et al. | 424/449 |
| 6,596,740 B2 | 7/2003 | Jones | 514/343 |
| 6,743,441 B2 | 6/2004 | Sanders et al. | 424/448 |
| 6,818,226 B2 | 11/2004 | Reed et al. | 424/449 |
| 6,828,336 B2 | 12/2004 | Walling | 514/343 |
| 6,911,475 B1 | 6/2005 | Cesaro et al. | 514/567 |
| 6,923,983 B2 | 8/2005 | Morgan et al. | 424/448 |
| 6,929,801 B2 | 8/2005 | Klose et al. | 424/448 |
| 6,951,846 B2 | 10/2005 | Hartell et al. | 514/58 |
| 6,995,265 B2 | 2/2006 | Comins et al. | 546/14 |
| 7,029,692 B1 | 4/2006 | Bracht | 424/449 |
| 7,030,104 B2 | 4/2006 | Gray et al. | 514/170 |
| 7,087,241 B2 | 8/2006 | Sanders et al. | 424/449 |
| 7,198,801 B2 | 4/2007 | Carrara et al. | 424/449 |
| 7,214,381 B2 | 5/2007 | Carrara et al. | 424/449 |
| 7,335,379 B2 * | 2/2008 | Carrara et al. | 424/449 |
| 7,425,340 B2 * | 9/2008 | Grenier et al. | 424/400 |
| 7,470,433 B2 | 12/2008 | Carrara et al. | 514/534 |
| 8,067,399 B2 | 11/2011 | Lehman et al. | 514/170 |
| 2001/0023261 A1 | 9/2001 | Ryoo | 514/772 |
| 2001/0031787 A1 | 10/2001 | Hsu et al. | 514/534 |
| 2001/0033870 A1 | 10/2001 | Luo et al. | 424/688 |
| 2001/0038855 A1 | 11/2001 | Desjardin et al. | 424/468 |
| 2002/0147236 A1 | 10/2002 | Sanders et al. | 514/540 |
| 2002/0150625 A1 | 10/2002 | Kryger | 424/489 |
| 2002/0183296 A1 | 12/2002 | Dudley et al. | 514/177 |
| 2003/0022877 A1 | 1/2003 | Dudley | 514/177 |
| 2003/0050292 A1 | 3/2003 | Dudley et al. | 514/177 |
| 2003/0095926 A1 | 5/2003 | Dugger, III | 424/43 |
| 2003/0139384 A1 | 7/2003 | Dudley | 514/177 |
| 2003/0143278 A1 | 7/2003 | DiPiano et al. | 424/489 |
| 2003/0147926 A1 | 8/2003 | Ebert et al. | 424/400 |
| 2003/0175329 A1 | 9/2003 | Azarnoff et al. | 424/449 |
| 2003/0181430 A1 | 9/2003 | Gray et al. | 514/170 |
| 2003/0199426 A1 | 10/2003 | Carrara et al. | 514/2 |
| 2003/0222105 A1 | 12/2003 | Lee et al. | 222/382 |
| 2003/0232072 A1 | 12/2003 | Dudley et al. | 424/449 |
| 2004/0002482 A1 | 1/2004 | Dudley et al. | 514/169 |
| 2004/0139990 A1 | 7/2004 | Wachter et al. | 134/25.4 |
| 2004/0192754 A1 | 9/2004 | Shapira et al. | 514/412 |
| 2004/0198706 A1 | 10/2004 | Carrara et al. | 514/169 |
| 2004/0213744 A1 | 10/2004 | Lulla et al. | 424/45 |
| 2004/0219197 A1 | 11/2004 | Carrara et al. | 424/449 |
| 2005/0142175 A1 | 6/2005 | Langguth et al. | 424/449 |
| 2006/0027278 A1 | 2/2006 | Kurmis | 140/123.5 |
| 2006/0153905 A1 | 7/2006 | Carrara et al. | 424/449 |
| 2006/0270642 A1 | 11/2006 | Lehman et al. | 514/170 |
| 2007/0048360 A1 | 3/2007 | Carrara et al. | 424/443 |
| 2007/0098775 A1 | 5/2007 | Carrara et al. | 424/449 |
| 2007/0166361 A1 | 7/2007 | Carrara et al. | 424/448 |

(56) References Cited

U.S. PATENT DOCUMENTS

| | | | |
|---|---|---|---|
| 2007/0225379 A1 | 9/2007 | Carrara et al. | 424/449 |
| 2008/0207737 A1 | 8/2008 | Zinger | 514/428 |
| 2009/0069364 A1 | 3/2009 | Carrara et al. | 514/284 |
| 2011/0245215 A1 | 10/2011 | Carrara et al. | 514/178 |

FOREIGN PATENT DOCUMENTS

| | | |
|---|---|---|
| EP | 0 491 803 B1 | 7/1992 |
| EP | 0 526 561 B1 | 2/1993 |
| EP | 0 643 963 B1 | 3/1995 |
| EP | 0 655 900 B1 | 6/1995 |
| EP | 0 672 422 A1 | 9/1995 |
| EP | 0 719 538 B1 | 7/1996 |
| EP | 0 785 211 A1 | 7/1997 |
| EP | 0 785 212 A1 | 7/1997 |
| EP | 0 802 782 B1 | 10/1997 |
| EP | 0 804 926 B1 | 11/1997 |
| EP | 0 811 381 A1 | 12/1997 |
| EP | 0 814 776 B1 | 1/1998 |
| EP | 0 859 793 B1 | 8/1998 |
| EP | 0 868 187 B1 | 10/1998 |
| EP | 1 089 722 B1 | 4/2001 |
| EP | 1 323 430 A2 | 7/2003 |
| EP | 1 323 431 A2 | 7/2003 |
| EP | 1 325 752 A2 | 7/2003 |
| FR | 2 518 879 A1 | 7/1983 |
| FR | 2 776 191 A1 | 9/1999 |
| JP | 9-176049 A | 7/1997 |
| WO | WO 90/11064 A1 | 10/1990 |
| WO | WO 92/08730 A1 | 5/1992 |
| WO | WO 94/06437 A1 | 3/1994 |
| WO | WO 95/18603 A1 | 7/1995 |
| WO | WO 95/29678 A1 | 11/1995 |
| WO | WO 97/03676 A1 | 2/1997 |
| WO | WO 97/29735 A1 | 8/1997 |
| WO | WO 97/34607 A1 | 9/1997 |
| WO | WO 97/38726 A2 | 10/1997 |
| WO | WO 98/17316 A1 | 4/1998 |
| WO | WO 98/37879 A1 | 9/1998 |
| WO | WO 99/20257 A1 | 4/1999 |
| WO | WO 99/24041 A1 | 5/1999 |
| WO | WO 99/48477 A1 | 9/1999 |
| WO | WO 00/01351 | 1/2000 |
| WO | WO 01/80796 A1 | 11/2001 |
| WO | WO 02/11768 A1 | 2/2002 |
| WO | WO 02/17967 A1 | 3/2002 |
| WO | WO 02/22132 A2 | 3/2002 |
| WO | WO 2004/037173 A2 | 5/2004 |
| WO | WO 2004/080413 A2 | 9/2004 |
| WO | WO 2005/039531 A1 | 5/2005 |

OTHER PUBLICATIONS

Julian E. Harrison, Adam C. Watkinson, Darren M. Green, Jonathan Hadgraft and Keith Brain, "The Relative Effect of Azone® and Transcutol® on Permeant Diffusivity and Solubility in Human Stratum Corneum", Pharmaceutical Research, vol. 13, No. 4, 542-546.*
PubMed Health. A service of the National Library of Medicine, National Institutes of Health. AHFS Consumer Medication Information. Bethesda (MD): American Society of Health-System Pharmacists; 2000-2011. Oxybutynin.*
Catherino et al., "Nomegestrol Acetate, a Clinically Useful 19-Norprogesterone Derivative which Lacks Estrogenic Activity," J. Steroid Biochem. Molec. Biol. 55(2):239-246 (1995).
Wang et al., "Transdermal Testosterone Gel Improves Sexual Function, Mood, Muscle Strength, and Body Composition Parameters in Hypogonadal Men," The Journal of Clinical Endocrinology & Metabolism 85(8):2839-2853 (2000).
www.rxlist.com (retrieved May 21, 2007).
U.S. Appl. No. 10/798,111, Non-Final Office Action dated Dec. 23, 2010.
U.S. Appl. No. 10/798,111, Non-Final Office Action dated Dec. 7, 2009.
U.S. Appl. No. 10/798,111, Non-Final Office Action dated Mar. 4, 2009.
U.S. Appl. No. 10/798,111, Non-Final Office Action dated Sep. 15, 2008.
U.S. Appl. No. 10/798,111, Non-Final Office Action dated Jun. 4, 2007.
U.S. Appl. No. 10/798,111, Non-Final Office Action dated Jan. 25, 2006.
U.S. Appl. No. 10/798,111 ,Non-Compliant Office Action dated Sep. 27, 2007.
U.S. Appl. No. 10/798,111, Final Office Action dated May 20, 2010.
U.S. Appl. No. 10/798,111, Final Office Action dated Jun. 5, 2009.
U.S. Appl. No. 10/798,111, Final Office Action dated Jun. 24, 2008.
U.S. Appl. No. 10/798,111, Final Office Action dated Jan. 12, 2007.
U.S. Appl. No. 10/798,111, Advisory Action dated Nov. 22, 2010.
U.S. Appl. No. 10/798,111, Advisory Office Action dated Sep. 9, 2009.
U.S. Appl. No. 11/441,311, Non-Final Office Action dated Dec. 23, 2010.
U.S. Appl. No. 11/441,311, Non-Final Office Action dated Sep. 22, 2009.
U.S. Appl. No. 11/441,311, Final Office Action dated Feb. 19, 2010.
U.S. Appl. No. 11/441,311, Advisory Office Action dated Jul. 28, 2010.
U.S. Appl. No. 11/755,923, Non-Final Office Action dated Oct. 12, 2010.
U.S. Appl. No. 11/755,923, Non-Final Office Action dated Feb. 22, 2010.
U.S. Appl. No. 11/755,923, Non-Final Office Action dated Mar. 19, 2009.
U.S. Appl. No. 11/755,923, Non-Final Office Action dated Nov. 17, 2008.
U.S. Appl. No. 11/755,923, Non-Final Office Action dated Jun. 24, 2008.
U.S. Appl. No. 11/755,923, Non-Final Office Action dated Mar. 10, 2008.
U.S. Appl. No. 11/755,923, Non-Final Office Action dated Sep. 7, 2007.
U.S. Appl. No. 11/755,923, Final Office Action dated Oct. 1, 2009.
U.S. Appl. No. 11/755,923, Final Office Action dated Jan. 25, 2008.
U.S. Appl. No. 11/755,923, Advisory Action dated Jan. 25, 2010.
U.S. Appl. No. 12/268,301, Non-Final Office Action dated Feb. 1, 2011.
English Abstract NLM2807923 XP-002337932 ,"Promoting Penetration of Locally Applied Substances by Urea".
Budavari et al., The Merk Index, 1996, Merck Research Laboratories, 12th Edition, pp. 253 and 269.
Kotiyan et al., "Eudragits:Role as crystallization inhibitors in drug-in-adhesive transdermal systems of estradiol," European Journal of Pharmaceutics and Biopharmaceutics 52: 173-180 (2001).
Lipp, "Selection and use of crystallization inhibitors for matrix-type transdermal drug-delivery systems containing sex steroids," J. Pharm. Pharmacol. 50: 1343-1349 (1998).
Moser et al., "Passive skin penetration enhancement and its quantification in vitro," European Journal of Pharmaceutics and Biopharmaceutics 52: 103-112 (2001).
Mura et al., "Evaluation of transcutol as a clonazepam transdermal permeation enhancer from hydrophilic gel formulations," European Journal of Pharmaceutical Sciences 9: 365-372 (2000).
D. Osborne et al., "Skin Penetration Enhancers Cited in the Technical Literature," Pharmaceutical Technology 1997, 21(11): 58-66.
R. Panchagnula et al., "Development and evaluation of an intracutaneous depot formulation of corticosteroids using transcutol as a cosolvent: in-vitro, ex-vivo and in-vivo rat studies," J. Pharm. Pharmacol. 1991, 43: 609-614.
L. Pavliv et al., "Topical formulation development of a novel thymidylate synthase inhibitor for the treatment of psoriasis," International Journal of Pharmaceutics 1994, 105: 227-233.
W.A. Ritschel et al., "In vitro skin penetration of griseofulvin in rat and human skin from an ointment dosage form," Arzneimittelforschung. 1988, 38(11): 1630-1632.

(56) References Cited

OTHER PUBLICATIONS

W.A. Ritschel et al., "Use of sorption promoters to increase systemic absorption of coumarin from transdermal drug delivery systems," Arzneimittelforschung, 1988, 38(12): 1774-1777.

W.A. Ritschel et al., "Development of an intracutaneous depot for drugs," Skin Pharmacol. 1991, 4:235-245.

J. Rojas, "Optimization of binary and ternary solvent systems in the percutaneous absorption of morphine base," S.T.P. Pharma Science 1991, I(1): 70-75.

G. Stüttgen, "Promoting penetration of locally applied substances by urea," Hautarzt 1989: 40 Suppl 9:27-31 (abstract).

K. Takahashi et al., "Effect of Vehicles on Diclofenac Permeation across Excised Rat Skin," Biol. Pharm. Bull. 1995, 18(4): 571-575.

E. Touitou, "Enhanced permeation of theophylline through the skin and its effect on fibroblast proliferation," International Journal of Pharmaceutics 1991, 70: 159-166.

A. Watkinson, "Aspects of the transdermal delivery of prostaglandins," International Journal of Pharmaceutics 1991, 74: 229-236.

A.C. Williams et al., "Urea Analogues in Proplyene Glycol as Penetration Enhancers in Human Skin," International Journal of Pharmaceutics 1989, 36: 43-50.

M. Yazdanian et al., "The effect of diethylene glycol monoethyl ether as a vehicle for topical delivery of invermectin," Veterinary Research Communications 1995, 19(4): 309-319.

P. Karande and S. Mitragotri, "High Throughput Screening of Transdermal Formulations," Pharmaceutical Research, 2002, 19(5): 655-660.

Oxytrol information sheet, Oxybutynin Transdermal System, Watson Pharma, Inc., Corona CA, 2 pages (Feb. 2003).

"New Drug Application: Elestrin, estradiol, Treatment for Postmenopausal Symptoms. BioSante Pharmaceuticals Announces Bio-E-Gel NDA Submission," Internet article, [online], Feb. 16, 2006; retrieved from the Internet: URL:http://www.drugs.com/nda/elestrin⎯060216.html (retrieved on Sep. 18, 2007).

J. Fang et al., XP-0007999490, "Effect of Adhesive and Drug reservoir on in vitro transdermal delivery of Nocotine," Pharmazie, Die, Govi Verlag, Eschborn, De, (1999), 54(2): 154-155.

Supplementary European Search Report, EP04719710, dated Feb. 8, 2012.

L. Jorgensen et al., XP023831877, "Toxicological and Absorption Enhancing Effects of Glycofurol 75 and Sodium Glycocholate in Monolayers of Human Intestinal Epithelial (Caco-2) Cells", International Journal of Pharmaceutics, vol. 95, No. 1-3, pp. 209-217 (2003).

Abstract: U. T. Lashmar et al., XP002668866, "Topical Application of Penetration Enhancers to the Skin of Nude Mice a Histopathological Study", Journal of Pharmacy and Pharmacology, vol. 41. No. 2, pp. 118-122 (1989).

Jan L. Shifren et al., "TransDermal Testosterone Treatment in Women With Impaired Sexual Function After Oophorectomy", The New England Journal of Medicine, vol. 343, pp. 682-688 (2000).

V. Davis SR and Burger HG, "Use of Androgens in Postmenopausal Women", Current Opinion in Obstetrics & Gynecology, vol. 9(3), pp. 177-180 (1997).

Barbara B. Sherwin et al., "Androgen Enhances Sexual Motivation in Females: A Prospective, Crossover Study of Sex Steroid Administration in the Surgical Menopause", Psychosomatic Medicine, vol. 47, No. 4, pp. 339-351 (1985).

U.S. Appl. No. 10/798,111, Advisory Action dated Jun. 30, 2011.

U.S. Appl. No. 10/798,111, Non-Final Office Action dated Feb. 3, 2012.

Irina Turchin et al., "Dermacase", vol. 51, Canadain Family Physician, pp. 503-506 (2005).

G.S. Mijnhout et al., "Oxybutynin: Dry Days for Patients With Hyperhidrosis", The Netherlands Journal of Medicine, Review vol. 64, No. 9, pp. 326-328 (2006).

Tanja Schlereth et al., "Hyperhidrosis—Causes and Treatment of Enhanced Sweating", Medicine Review Article, Deutsches Arzteblatt International, vol. 106 (3), pp. 32-37 (2009).

Barbara Togel et al., "Current Therapeutic Strategies For Hyperhidrosis: A Review", European Journal of Dermatology. vol. 12, No. 3, pp. 219-223, (2002).

U.S. Appl. No. 11/268,301, Non-Final Office Action, dated Oct. 17, 2012.

U.S. Appl. No. 13/106,715, Non-Final Office Action, dated Oct. 1, 2012.

U.S. Appl. No. 13/044,447, Non-Final Office Action, dated Oct. 2, 2012.

US 6,214,374, 04/2001, Schmirier et al. (withdrawn)

* cited by examiner 24-hour *In Vitro* Comparative Permeation Study of Two Compositions Out of the Scope of the Present Invention Versus a Marketed Product 24-hour *In Vitro* Comparative Flux Profiles of a Composition of the present invention versus two Compositions out of the scope of the present invention 24-hour *In Vitro* Comparative Flux Profiles of a Composition of the present invention versus two Compositions out of the scope of the present invention

TRANSDERMAL COMPOSITIONS FOR ANTICHOLINERGIC AGENTS

CROSS-REFERENCE TO RELATED APPLICATIONS

This application is a continuation-in-part of application Ser. No. 10/798,111 filed Mar. 10, 2004 which claims the benefit of U.S. provisional patent application 60/510,613 filed Oct. 10, 2003 and U.S. provisional patent application 60/453,604 filed Mar. 11, 2003, and a continuation-in-part of application Ser. No. 11/755,923 filed May 31, 2007, which is a continuation-in-part of U.S. patent application Ser. No. 11/371,042 filed Mar. 7, 2006, now U.S. Pat. No. 7,335,379, which is a continuation of International application no. PCT/EP2004/011175 filed Oct. 6, 2004, which claims the benefit of U.S. provisional patent application No. 60/510,613, filed Oct. 10, 2003. Application Ser. No. 11/755,923 is also a continuation-in-part of U.S. patent application Ser. No. 11/634,005 filed Dec. 4, 2006, now U.S. Pat. No. 7,404,965, which is a continuation of application Ser. No. 10/343,570 filed May 19, 2003, now U.S. Pat. No. 7,214,381, which is the U.S. national stage of International application no. PCT/EP01/09007 filed Aug. 3, 2001. Each prior application is expressly incorporated herein in its entirety by reference thereto.

TECHNICAL FIELD

This invention relates generally to formulations for the transdermal delivery of anti-cholinergic agents, typically oxybutynin, and more particularly to topical formulations of oxybutynin that contain a novel delivery vehicle and that are substantially free of long chain fatty alcohols, long chain fatty acids, and long-chain fatty esters.

This invention also relates to methods for treating overactive bladder and urinary incontinence using such formulations.

BACKGROUND OF THE INVENTION

Topical or transdermal delivery systems for the administration of drugs are known to offer several advantages over oral delivery of the same drugs. Generally, the advantages of topical or transdermal delivery of drugs relate to pharmacokinetics. More specifically, one common problem associated with the oral delivery of drugs is the occurrence of peaks in serum levels of the drug, which is followed by a drop in serum levels of the drug due to its elimination and possible metabolism. Thus, the serum level concentrations of orally administered drugs have peaks and valleys after ingestion. These highs and lows in serum level concentrations of drug often lead to undesirable side effects.

In contrast, topical and transdermal delivery of drugs provides a relatively slow and steady delivery of the drug. Accordingly, unlike orally administered drugs, the serum concentrations of topically or transdermally delivered drugs are substantially sustained and do not have the peaks associated with oral delivery.

The sustained serum concentrations associated with topical or transdermal drug delivery avoids the systemic side effects of oral administration of drugs. Specifically, first pass metabolism of the drug by the liver is circumvented by utilizing transdermal or topical delivery vehicles for the administration of drugs.

For example, there is a significant decrease in adverse effects associated with the transdermal delivery of oxybutynin. Oxybutynin is an antispasmodic, anticholinergic agent. Oxybutynin is administered as a racemate of R- and S-isomers. Chemically, oxybutynin is d,l (racemic) 4-diethylamino-2-butynyl phenylcyclohexylglycolate. The empirical formula of oxybutynin is $C_{22}H_{31}NO_3$. Oxybutynin has been found to have a direct antispasmodic effect on smooth muscle and inhibits the muscarinic action of acetylcholine on smooth muscle, but exhibits only one-fifth of the anticholinergic activity of atropine detrusor muscle (effect observed in rabbits), and four to ten times its antispasmodic activity. Oxybutynin has not been found to possess blocking effects at skeletal neuromuscular junctions or autonomic ganglia (antinicotinic effects). Moreover, oxybutynin has been found to relax bladder smooth muscle.

In patients with conditions characterized by involuntary bladder contractions, cystometric studies have demonstrated that oxybutynin increases bladder (vesical) capacity, diminishes the frequency of uninhibited contractions of the detrusor muscle, and delays the initial desire to void. Oxybutynin thus decreases urgency and the frequency of both incontinent episodes and voluntary urination. It has also been reported that antimuscarinic activity resides predominantly in the R-isomer. Oral oxybutynin is widely used for the relief of symptoms of bladder instability associated with voiding in patients with uninhibited neurogenic or reflex neurogenic bladder, i.e., urgency, frequency, urinary leakage, urge incontinence, and dysuria.

Until recently oral anticholinergic medications have been the primary pharmacotherapy for the treatment of urge urinary incontinence and overactive bladder (OAB), among which oxybutynin is the golden standard medication. There are several different drug products available on the international market for oral administration of oxybutynin, including immediate- and extended-release formulations. Both have been shown to be effective in the treatment of OAB. However, their compliance has been limited by anticholinergic side effects. Adverse reactions associated with oxybutynin therapy, however, may include cardiovascular manifestations such as palpitations, tachycardia or vasodilatation; dermatologic manifestations such as decreased sweating, rash; gastrointestinal and genitourinary manifestations such as constipation, decreased gastrointestinal motility, dry mouth, nausea, urinary hesitance and retention; nervous system manifestations such as asthenia, dizziness, drowsiness, hallucinations, insomnia, restlessness; opthalmic manifestations such as amblyopia, cycloplegia, decreased lacrimation, mydriasis. Most common side effects associated with oral oxybutynin encompasses dry mouth, dizziness, blurred vision, and constipation. These adverse experiences may be uncomfortable enough to substantially limits long-term patient compliance (<18% at 6 months). Oral formulations of oxybutynin indeed undergo hepatic metabolism to form N-desethyloxybutynin (DEO), which is considered to be the primary underlying cause of dry mouth associated with anticholinergic therapy. See Appell R. A., Chancellor M. B., Zobrist R. H., Thomas H., Sanders S. W., "Pharmacokinetics, metabolism, and saliva output during transdermal and extended-release oral oxybutynin administration in healthy subjects", Mayo Cline Proc. 78: 696-702; 2003, the entire content of which is herein incorporated as reference. See also Kelleher C. J., Cardozo L. D., Khullar V., Salvatore S., "A medium-term analysis of the subjective efficacy of treatment for women with detrusor instability and low bladder compliance.", Br J Obstet Gynaecol. 104: 988-93; 1997, the entire content of which is herein incorporated as reference.

The development of an extended-release formulation of oxybutynin was intended to preserve the efficacy of the drug while reducing the incidence and severity of dry mouth and other anticholinergic side effects. Extended-release formulations allow once-a-day dosing and provide a more consistent therapeutic drug level in the blood throughout the day and less metabolite generation. This lower DEO metabolite generation is associated with reduced adverse effects. Recently, a transdermal patch of oxybutynin (OXYTROL®, Watson Pharmaceuticals, Inc.) has entered the marketplace as a therapeutic option for OAR Transdermal administration of oxybutynin leads to clinically important changes in the pharmacokinetics, metabolism, and pharmacodynamic effects of oxybutynin compared with extended-release oral treatment. Transdermal administration of oxybutynin, as any other route of administration avoiding gastrointestinal and hepatic first-pass metabolism, results in lower fluctuation in oxybutynin plasmatic levels, in reduced DEO metabolite formation, and in increased saliva production. Lower DEO plasma concentrations and greater saliva output are thought to correspond to the reported low incidence of dry mouth in patients treated with transdermal oxybutynin. See, Dmochowski R R, Davila G W, Zinner N R, Gittelman M C, Saltzstein D R, Lyttle S, Sanders S W; For The Transdermal Oxybutynin Study Group.; "Efficacy and safety of transdermal oxybutynin in patients with urge and mixed urinary incontinence", The Journal of Urology, Vol. 168, 580-586, August 2002, the entire content of which is herein incorporated as reference. Phase III studies comparing OXYTROL® patch to oral extended-release tablet (DITROPAN® XL, Ortho McNeil Janssen) showed that only 4.1% of the patients on transdermal therapy reported dry mouth, whereas 60.8% of the patients on oral treatment reported this side effect. This reduction of incidence of dry mouth, together with the improvement of overactive bladder symptoms, is responsible for a better quality of life seen in patients treated with transdermal oxybutynin compared to oral oxybutynin therapy. Thus, it can be easily seen that transdermal delivery of oxybutynin has been shown to be more advantageous, as well as preferred over oral delivery of oxybutynin.

However, although the transdermal and/or transmucosal delivery of oxybutynin overcome some of the problems associated with oral administration of oxybutynin, such as that described above, this route of administration is not free of its own drawbacks. Transdermal patches very often cause allergic reactions and skin irritations due to their occlusive nature, or due to their composition (incompatibility reactions with the polymers used). In the OXYTROL® phase III study, 16.8% of the patients reported itching at the patch application site as an adverse effect. A transdermal oxybutynin gel should combine the advantages of the transdermal route (reduced side effects related avoidance of first-pass metabolism leading to lowered formation of DEO metabolite; steady plasmatic levels) with a low potential for skin irritation. Since an oxybutynin gel would be applied directly to the skin, skin reactions associated with the adhesive properties and the occlusive nature of transdermal patch formulations (e.g. OXYTROL®) should be avoided.

Besides skin irritation and tolerance considerations, another issue of transdermal drug delivery systems is that these systems are typically restricted to low-molecular weight drugs and those with structures having the proper lipophilic/hydrophilic balance. High molecular weight drugs, or drugs with too high or too low hydrophilic balance, often cannot be incorporated into current transdermal systems in concentrations high enough to overcome their impermeability through the stratum corneum. Efforts have been made in the art to chemically modify the barrier properties of skin to permit the penetration of certain agents (since diffusion is primarily controlled through the stratum corneum), enhance the effectiveness of the agent being delivered, enhance delivery times, reduce the dosages delivered, reduce the side effects from various delivery methods, reduce patient reactions, and so forth. In this regard, penetration enhancers have been used to increase the permeability of the dermal surface to drugs. Various permeation enhancers have been reported as being effective for the transdermal or topical delivery of oxybutynin. For example, U.S. Pat. Nos. 5,411,740, 5,500,222, and 5,614,211, each disclose monoglyceride or a mixture of monoglycerides of fatty acids as the preferred permeation enhancer for an oxybutynin transdermal therapeutic system. U.S. Pat. No. 5,736,577 describes a pharmaceutical unit dosage form for transdermal administration of (S)-oxybutynin comprising a permeation enhancer. U.S. Pat. Nos. 5,834,010 and 6,555,129 both disclose triacetin as a permeation enhancer for oxybutynin. U.S. Pat. No. 5,747,065 discloses monoglycerides and esters of lactic acid as a permeation enhancing mixture for oxybutynin. U.S. Pat. No. 5,843,468 describes a dual permeation enhancer mixture of lauryl acetate and a glycerol monolaurate for transdermal administration of oxybutynin. U.S. Pat. No. 6,004,578 disclose permeation enhancers selected from the group consisting of alkyl or aryl carboxylic acid esters of polyethyleneglycol monoalkyl ether, and polyethyleneglycol alkyl carboxymethyl ethers for a transdermal matrix drug delivery device comprising oxybutynin. Meanwhile, U.S. Pat. No. 6,267,984 discloses skin permeation enhancer compositions comprising a monoglyceride and ethyl palmitate for transdermal delivery of oxybutynin. U.S. Pat. No. 6,562,368 discloses the use of hydroxide-releasing agent to increase the permeability of skin or mucosal tissue to transdermally administered oxybutynin. U.S. Pat. Nos. 7,029,694 and 7,179,483 relate to oxybutynin gel formulations that include permeation enhancers as optional components, among which triacetin and monoglycerides are preferred permeation enhancers.

The most common penetration enhancers, however, are toxic, irritating, oily, odiferous, or allergenic. Specifically, the penetration enhancers used and thought to be necessary to transdermally deliver oxybutynin, namely, long-chain acids such as lauric acid and oleic acid, long-chain alcohols such as lauryl or myristyl alcohol, and long-chain esters such as triacetin (the glycerol trimester of acetic acid), glycerol monolaurate or glycerol monooleate, tend to include aliphatic groups that make the formulations oily and malodorous.

Thus, there is a need in the industry for a transdermal formulation that adequately delivers oxybutynin to patients with skin tolerability, but does not include the unpleasant odor common to the prior art formulations.

SUMMARY OF INVENTION

The present invention relates to transdermal or transmucosal malodorous-free and irritation-free formulations comprising oxybutynin and a delivery vehicle. In particular, the formulation comprises an anti-cholinergic agent of oxybutynin, typically in an amount between about 0.06 to 5% by weight of the composition; and a delivery vehicle which comprises a C2 to C4 alkanol, a polyalcohol, and a monoalkyl ether of diethylene glycol present in relative amounts sufficient to provide permeation enhancement of oxybutynin through mammalian dermal or mucosal surfaces. The formulation is substantially free of long-chain fatty alcohols, long-chain fatty acids and long-chain fatty esters in order to avoid potential undesirable odor and irritation effects caused by such compounds during use of the formulation. Thus, advantageously, the formulations of the present invention do not include the undesirable odor-causing and irritation-causing permeation enhancers that were once thought to be necessary for such transdermal or transmucosal formulations.

In accordance with the invention, the alkanol may be present in an amount between about 45% to 75% by weight of the vehicle. The alkanol may be ethanol, isopropanol, n-propanol, and mixtures thereof. Preferably, the alkanol is ethanol. The polyalcohol may be advantageously present in an amount between about 1% and 30% by weight of the vehicle. The polyalcohol may be polyethylene glycols having general formula $CH_2OH(CH_2OH)_nCH_2OH$ wherein the number of oxyethylene groups represented by n is between 4 to 200, propylene glycol, dipropylene glycol, butylene glycol, hexylene glycol, glycerin, and mixtures thereof. Preferably, the polyalcohol is propylene glycol. The monoalkyl ether of diethylene glycol may be present in an amount of about 1% and 15% by weight of the vehicle. The monoalkyl ether of diethylene glycol may be diethylene glycol monoethyl ether, diethylene glycol monomethyl ether, and mixtures thereof. Preferably, the monoalkyl ether of diethylene is diethylene glycol monoethyl ether. In accordance with the invention, oxybutynin may be present in an amount between about 0.1% to 20% by weight of the vehicle, preferably in an amount between about 2% by weight of the vehicle. Oxybutynin may be present as the free base or as a pharmaceutically acceptable salt thereof. Examples of salt comprise, but are not limited to, acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate. Preferably, oxybutynin is present as free base or as the hydrochloride salt. If desired, oxybutynin may be present in combination with a secondary active agent for concurrent administration subject to the previously stated provision.

The formulation can further include at least one of a gelling agent, neutralizing agent, buffering agent, moisturizing agent, humectant, surfactant, antioxidant, emollient, film-forming agent, or buffer, and the like.

The formulation may be applied directly to the skin such as by, for example and not limitation, a gel, a foam, an ointment, a liposomal emulsion, a microemulsion, a nanoemulsion, a suspension, or a lacquer and the like, or other passive or active transdermal devices for absorption through the skin or mucosal surface. In a preferred aspect of the invention, the formulation is a gel.

The present invention further provides a method for treating overactive bladder or urge and urinary incontinence in a subject, the method comprising administering to a subject in need thereof, a topical or transdermal composition of oxybutynin according to the present invention.

Advantageously, the composition of the present invention provides a steady plasma concentration of oxybutynin to a subject administered with the composition, as well as avoiding undesirable peaks in drug concentration, and/or reduces the incidences of unwanted, undesirable side effects such as dry mouth, accommodation disturbances, nausea and dizziness.

The oxybutynin composition of the present invention provides a sustained transdermal oxybutynin flux allowing therapeutic levels of oxybutynin for at least 24 hours, preferably for at least 48 hours and most preferably for at least 72 hours. Thus, the composition only needs to be administrated once per day, once every other day, once every third day or twice per week.

DETAILED DESCRIPTION OF THE PREFERRED EMBODIMENTS

Figure 1:
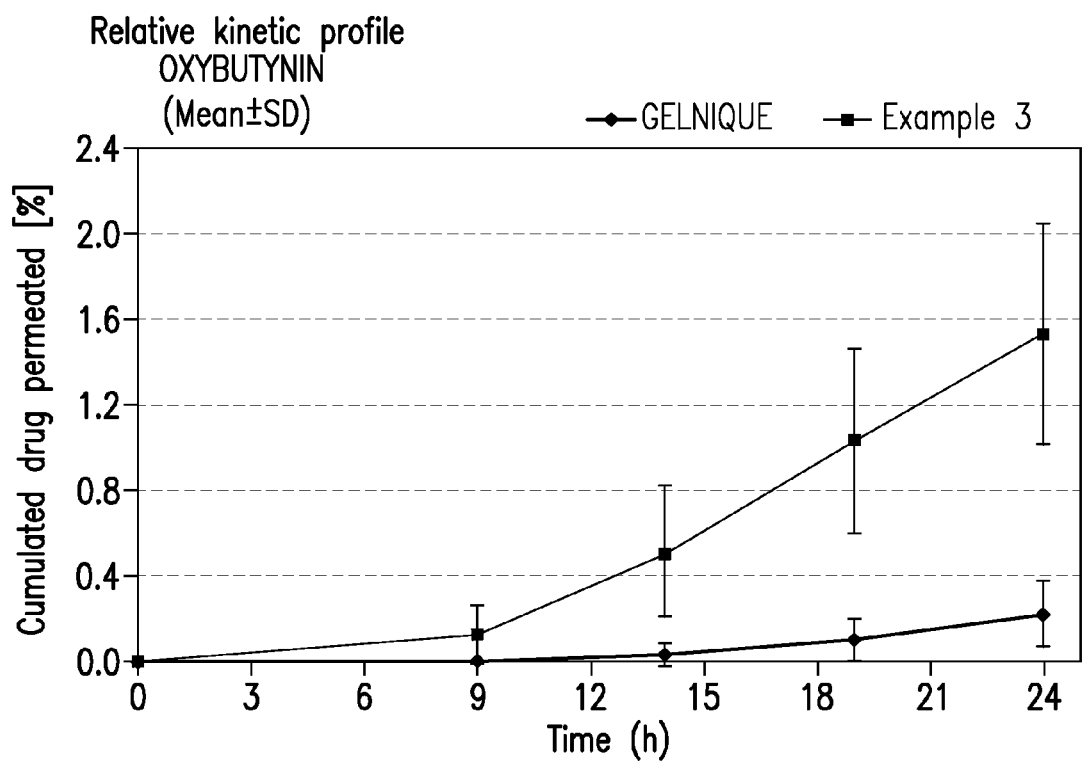
FIG. 1 is a graph illustrating the results from an in-vitro 24-hour comparative permeation study comparing permeation of a composition comprising oxybutynin of the present invention, and a marketed product.

The present invention relates generally to compositions or formulations that contain an anti-cholinergic agent, preferably oxybutynin, for administration to subjects in need thereof. The invention further relates to formulations for the transdermal or transmucosal administration of oxybutynin that are substantially free of malodorous, and irritation-causing permeation enhancers. Surprisingly, the formulation of the present invention can achieve sufficient absorption to result in an effective dosage of oxybutynin circulating in serum without the inclusion of the malodorous and irritation-causing permeation enhancers that have been used to date. In a preferred aspect of the invention, the formulation is a clear, water-washable, quick-drying, spreadable, non-greasy, non-occlusive topical gel of oxybutynin which is free of fatty permeation enhancers.

Advantageously, the substantial omission of the long-chain fatty alcohols, long-chain fatty acids, and long-chain fatty esters provides a formulation that does not have the unpleasant odor, irritation, and/or greasy texture caused by formulations of the prior art that include one or more of such compounds. Thus, the formulation in accordance with the present invention will result in greater patient compliance. The inventive formulations are substantially free of such alcohols, acids, and esters so that the odors associated with those compounds do not emanate from the formulation. In this regard, "substantially free" means an amount which does not impart a perceptible odor to the formulation at a distance of one meter. Such formulations are also deemed to be substantially odor-free. For the purpose of example and illustration, a formulation comprising fatty alcohols, fatty acids and/or fatty esters in an amount of less than about 0.1% by weight of the formulation is substantially odor-free.

In accordance with the invention, oxybutynin is present as the free base or as a salt. For purpose of illustration but not limitation, examples of some pharmaceutically acceptable salts of oxybutynin are acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate. The oxybutynin may be present as a racemate, as a pure single isomer, or as a mixture of S enantiomer and R enantiomers. Pharmaceutical derivatives of oxybutynin which are close-related to oxybutynin are also understood to fall within the scope of the present invention.

In accordance with the invention, the delivery vehicle of the present invention preferably comprises a C2 to C4 short-chain alkanol, a polyalcohol, and a monoalkyl ether of diethylene glycol in an amount sufficient to provide permeation enhancement of the oxybutynin through mammalian dermal or mucosal surfaces. For the purpose of illustration and not limitation, the alkanol may be ethanol, isopropanol, or n-propanol. The alkanol is preferably ethanol. The alkanol is present in an amount between about 45 to 75% w/w, preferably between about 50% to 70%, and more preferably between about 55% and 65% w/w. As known in the art, the amount of the alkanol may be selected to maximize the diffusion of the active agent through the skin while minimizing any negative impact on the active agent itself or desirable properties of the formulation. The alkanol can be present in a mixture with water. The polyalcohol is advantageously present in an amount between about 1% and 30% of the vehicle, preferably from 2.5% to 20% w/w, and more preferably from about 5% to 10% w/w. The monoalkyl ether of diethylene glycol is present in an amount of about 1% and 15%, preferably between about 2.5% to 10% w/w and more preferably between about 2.5% to 5% w/w.

The formulation may further include a thickening agent or gelling agent present in an amount sufficient to alter the viscosity of the formulation. A gelling agent can be selected from the group including: carbomer 980 or 940 NF, 981 or 941 NF, 1382 or 1342 NF, 5984 or 934 NF, ETD 2020, 2050, 934P NF, 971P NF, 974P NF, Noveon AA-1 USP; cellulose derivatives such as ethylcellulose, hydroxypropylmethylcellulose (1-IPMC), ethylhydroxyethylcellulose (EHEC), carboxymethylcellulose (CMC), hydroxypropylcellulose (HPC) (Klucel grades), hydroxyethylcellulose (HEC) (Natrosol grades), HPMCP 55, Methocel grades; natural gums such as arabic, xanthan, guar gums, alginates; polyvinylpyrrolidone derivatives such as Kollidon grades; polyoxyethylene polyoxypropylene copolymers such as Lutrol F grades 68, 127. Other gelling agents include chitosan, polyvinyl alcohols, pectins, veegum grades. A tertiary amine, such as triethanolamine or trolamine, can be included to thicken and neutralize the system. The amount and the type of the gelling agent in the formulation may be selected by the man skilled in the art to provide the desired product consistency and/or viscosity to facilitate application to the skin. The gelling agent is present from about 0.2 to about 30% w/w of the formulation depending on the type of polymer. For example, the gelling agent is preferably present in an amount between about 0.3% to 2% for carbomers, and between about 1% to 5% for hydroxypropylcellulose derivatives.

The formulation may further include preservatives such as, but not limited to, benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid, derivatives thereof and the like. The preservative is present from about 0.01 to about 10% w/w depending on the type of compound.

The formulation may further include antioxidants such as but not limited to, tocopherol, ascorbic acid, butylated hydroxyanisole, butylated hydroxytoluene, fumaric acid, malic acid, propyl gallate, sulfites, derivatives thereof and the like. The antioxidant is present from about 0.001 to about 5.0% w/w of the formulation depending on the type of compound.

The formulation may further include a buffer such as carbonate buffers, citrate buffers, phosphate buffers, acetate buffers, hydrochloric acid, lactic acid, tartric acid, diethylamine, triethylamine, diisopropylamine, aminomethylamine. Although other buffers as known in the art may be included. The buffer may replace up to 100% of the water amount within the formulation.

The formulation may further include a humectant. The formulation may further include humectant, such as but not limited to glycerin, propylene, glycol, sorbitol, triacetin. The humectant is present from about 1 to 10% w/w of the formulation depending on the type of compound.

The formulation may further include a sequestering agent such as edetic acid. The sequestering agent is present from about 0.001 to about 5% w/w of the formulation depending on the type of compound.

The formulation may further include anionic, non-ionic or cationic surfactants. The surfactant is present from about 0.1% to about 30% w/w of the formulation depending on the type of compound.

The formulation may further include a pH regulator, generally, a neutralizing agent, which can optionally have crosslinking function. By way of example and not limitation, the pH regulator may include a ternary amine such as monoethanolamine, diethanolamine, triethanolamine, tromethamine, tetrahydroxypropylethylendiamine, aminomethyl propanol, diisopropanolamine, or an inorganic alkali such as NaOH solution, KOH solution, or $NH_4OH$ solution. The pH regulator is present in the formulations in variable amounts depending on the nature and the relative strength of the pH regulator. The optimum pH may also be determined and may depend on, for example, the nature of the active agent and the degree of flux required.

The formulation may further include moisturizers and emollients to soften and smoothen the skin or to hold and retain moisture. By way of example and not limitation, moisturizers and emollients may include cholesterol, lecithin, light mineral oil, petrolatum, and urea.

For any particular formulation, the active agent of oxybutynin and other ingredients may be selected to achieve the desired drug delivery profile and the amount of penetration desired.

Although oxybutynin is the preferred anti-cholinergic agent that is disclosed herein, other such agents, among which those having an antimuscarinic activity are preferred, can be used in place of oxybutynin. Preferred anti-cholinergic drugs with antimuscarinic activity include, without limitation, tolterodine, trospium, propiverine, flavoxate, emepronium, propantheline, darifenacin, and solifenacin.

In a preferred embodiment, the composition is provided as a topical, non-occlusive gel. In particular, the composition comprises oxybutynin free base in an amount of about 3% by weight of the composition; and the delivery system comprises anhydrous ethanol in an amount of about 50.72% by weight of the composition, propylene glycol in an amount of about 20% by weight of the composition, monoethyl ether of diethylene glycol in an amount of about 2.5% by weight of the composition, hydrochloric acid to provide a pH of about 6 to 9, hydroxypropylcellulose in an amount of about 1 to 2% by weight of the composition, butylhydroxytoluene in an amount of about 0.05% by weight of the composition, and water quantum sufficit. Alternatively, the composition can include oxybutynin as a hydrochloride salt in an amount between about 5 to 15% by weight of the composition; and the delivery system comprises ethanol, isopropanol, or a mixture thereof in an amount between about 50 to 70% by weight of the composition; propylene glycol in an amount between about 1 to 10% by weight of the composition; a monoethyl ether of diethylene glycol in an amount between about 1 to 5% by weight of the composition, and water. Preferably, the composition is administered to a patient in need thereof by the means of a metered-dose dispenser. Between 1 and 5 grams is typically applied over a skin surface of 100 to 1500 cm$^2$ and preferably between about 2.5 grams and 3.0 grams of gel is applied over a skin surface of about 500 to 1000 cm$^2$.

Another preferred composition comprises a gel composition of oxybutynin hydrochloride in an amount of about 10% by weight of the composition; and the delivery system comprises anhydrous ethanol in an amount of about 60% by weight of the composition, propylene glycol in an amount between about 1 to 10% by weight of the composition, monoethyl ether of diethylene glycol in an amount between about 1 to 5% by weight of the composition, sodium hydroxide to provide a pH of about 4 to 7, hydroxypropylcellulose in an amount of about 1 to 2% by weight of the composition, butylhydroxytoluene in an amount between about in an amount of about 0 to 0.05% by weight of the composition, and water quantum sufficit. About 0.5 to 2 grams of this composition is dispensed from a multiple-dose container; and applied over a skin surface between 50 and 500 cm$^2$, preferably 1 gram of gel is applied over a skin surface of about 150 to 350 cm$^2$.

The invention also relates to a method for administering oxybutynin to a mammal in need thereof comprising topically or transdermally administering to the skin or the mucosa of a mammal one of the compositions disclosed herein. Preferably, the mammal is a human. For example, the treatments methods include treating hyperactivity of the detrusor muscle with frequent urge to urinate, increased urination during the night, urgent urination, involuntary urination with or without the urge to urinate, painful or difficult urination, detrusor hyperreflexia and detrusor instability. Typically, not more than 200 mg of oxybutynin is administered per day, with a daily dose of oxybutynin between about 40 and about 100 mg being preferred. The composition is advantageously administered upon the abdomen, shoulder, arm, or thigh of the subject.

A more preferred daily dosage of oxybutynin is between 0.06 and 0.18 mcg per cm$^2$ and is dispensed from a unidose container or from a multiple-dose container for a duration of from about 24 to about 72 hours. The application of the composition may be made on the same or a different site on consecutive days. Advantageously, the application of the composition is rotated between shoulder, thigh, abdomen, and arm on consecutive days.

In certain preferred embodiments of the present invention, the formulation may have the following formulae as shown in Tables 1 to 4 herein.

TABLE 1

| | |
|---|---|
| Oxybutynin (expressed as free base) | 0.1-20% w/w |
| Short-chain alkanol | 45-75% w/w |
| Polyalcohol | 1-30% w/w |
| Diethylene glycol mono alkyl ether | 1-15% w/w |
| Thickening agent | 0.2-30% w/w |
| pH adjusting agent | qs pH 4-9 |
| Purified water | q. ad. 100% w/w |

TABLE 2

| | |
|---|---|
| Oxybutynin free base | 1-10% w/w |
| Ethanol (expressed as absolute) | 45-75% w/w |
| Propylene glycol | 1-30% w/w |
| Diethylene glycol mono ethyl ether | 1-15% w/w |
| Carbomer | 0.3-2% w/w |
| pH adjusting agent | qs pH 5-8 |
| Purified water | q. ad. 100% w/w |

TABLE 3

| | |
|---|---|
| Oxybutynin free base | 1-10% w/w |
| Ethanol (expressed as absolute) | 45-75% w/w |
| Propylene glycol | 1-30% w/w |
| Diethylene glycol mono ethyl ether | 1-15% w/w |
| Hydroxypropylcellulose | 0.5-2% w/w |
| pH adjusting agent | qs pH 5-8 |
| Purified water | q. ad. 100% w/w |

TABLE 4

| | |
|---|---|
| Oxybutynin Hydrochloride | 5-15% w/w |
| Ethanol (expressed as absolute) | 45-75% w/w |
| Propylene glycol | 1-30% w/w |
| Diethylene glycol mono ethyl ether | 1-15% w/w |
| Hydroxypropylcellulose | 0.5-2% w/w |
| pH adjusting agent | qs pH 5-8 |
| Purified water | q. ad. 100% w/w |

The formulation of the present invention is advantageous at least for the following reasons. First, the formulations of the present invention are substantially free of long-chain fatty alcohols, long-chain fatty acids, and long-chain fatty esters. Surprisingly, the formulations exhibit skin penetration sufficient to deliver an effective dosage of oxybutynin to the user. This is an unexpected advantage that those of ordinary skill in the art would not have readily discovered since it had been generally understood that permeation enhancers, and more particularly long-chain fatty alcohols, long-chain fatty acids, and long chain fatty esters, would be required to enhance skin penetration of oxybutynin to permit an effective dose to penetrate the skin. Second, because the formulation does not include aliphatic acid groups, such as fatty acids, that are commonly included in topical gels, it does not have the odor or oily texture which is associated with that ingredient as in presently-available gels. Numerous studies acknowledge the irritation-causing potential of unsaturated fatty acids such as oleic acid. See, Tanojo H. Boelsma E, Junginger H E, Ponce M, Bodde H E, "In vivo human skin barrier modulation by topical application of fatty acids," Skin Pharmacol Appl. Skin Physiol. 1998 March April; 11 (2) 87 97. Third, the absence of long-chain fatty alcohols, long-chain fatty acids, and long-chain fatty esters means that the irritation potential is lower and that there is less chance for the components to interact, reducing the need for stabilizers in the formulation. It is to be understood, however, that if such stabilizers are desired, the invention encompasses formulations which include antioxidants, chelators or preservatives. The reduction in the number of ingredients is advantageous at least in reducing manufacturing costs, possible skin irritation. Additionally, the reduced number of ingredients increases the storage stability of the formulation by decreasing the chance that the ingredients will interact prior to being delivered to the patient in need thereof. This does not, however, imply that additional ingredients cannot be included in the formulation for particular aesthetic and/or functional effects. For example, the formulation may optionally include one or more moisturizers for hydrating the skin or emollients for softening and smoothing the skin. Glycerin is an example of such a suitable moisturizing additive.

The formulation may be applied once daily, or multiple times per day depending upon the condition of the patient. The formulation of the invention may be applied topically to any body part, such as the thigh, abdomen, shoulder, and upper arm. In one embodiment, up to 10 grams of a formulation in the form of a gel is applied to an area of skin. In a preferred embodiment of the invention, not more than 5 grams of a formulation in the form of a gel is applied to about an area of skin for about 1 g of gel. In a most preferred embodiment of the invention, about 1 to 3 grams of a formulation in the form of a gel is applied to about a 100 square-centimeter to a 1000 square-centimeter area of skin. Formulation of the present invention may be applied on alternate areas of the body as applications alternate. For example, the gel may be applied to the abdomen for the first application, the upper arm for the second application, and back to the abdomen for the third application. This may be advantageous in alleviating any sensitivity of the skin to repeated exposure to components of the formulation. Alternatively, the formulation of the present invention may be applied always on the same area of the body.

The invention includes the use of the formulations described above to treat subjects to increase circulating levels of oxybutynin within the patient. Preferred dosage units are capable of delivering an effective amount of oxybutynin over a period of about 24 hours. By an "effective" or "therapeutically effective" amount of oxybutynin is meant a nontoxic, but sufficient amount of oxybutynin to provide the desired effect. However, it will be appreciated by those skilled in the art that the desired dose will depend on the specific form of oxybutynin as well as on other factors; the minimum effective dose of each form of oxybutynin is of course preferred to minimize the side effects associated treatment with oxybutynin. The formulation is preferably applied on a regularly-timed basis so that administration of oxybutynin is substantially continuous.

The composition may be applied directly or indirectly to the skin or mucosal surfaces. Preferably, the composition is non occlusive. The phrase "non-occlusive" as used herein refers to a system that does not trap nor segregate the skin from the atmosphere.

The composition of the invention can be in a variety of forms suitable for transdermal or transmucosal administration. For purpose of illustration and not limitation, the various possible forms for the present composition include gels, ointments, creams, lotions, microspheres, liposomes, micelles, foams, lacquers, non-occlusive transdermal patches, bandages, or dressings, or combinations thereof. Alternatively, the composition may be in the form of a spray, aerosol, solution, emulsion, nanosphere, microcapsule, nanocapsule, as well as other topical or transdermal forms known in the art. In a preferred embodiment, the invention is a gel, a lotion, or a cream. In a most preferred embodiment, the invention is a non-occlusive gel. Gels are semisolid, suspension-type systems. Single-phase gels comprise macromolecules (polymers) distributed substantially uniformly throughout the carrier liquid, which is typically aqueous. However, gels preferably comprise alcohol and, optionally, oil. Preferred polymers, also known as gelling agents, are crosslinked acrylic acid polymers, polyethylene oxides, polyoxyethylene-polyoxypropylene copolymers and polyvinylalcohol; cellulosic polymers (hydroxypropyl cellulose, hydroxyethyl cellulose, hydroxypropyl methylcellulose, hydroxypropyl methylcellulose phthalate, methyl cellulose); gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

The compositions of the present invention may be manufactured by conventional techniques of drug formulation, particularly topical and transdermal drug formulation, which are within the skill of the art. Such techniques are disclosed in "Encyclopedia of Pharmaceutical Technology, $2^{nd}$ Ed., edited by I. Swarbrick and J. C. Boylan, Marcel Dekker, Inc., 2002, the content of which is incorporated herein by reference.

The invention provides a composition for the transdermal administration of oxybutynin which is useful in a variety of contexts, as will be readily appreciated by those skilled in the art. For example, oxybutynin has been indicated for the treatment of hyperactivity of the detrusor muscle (over activity of the bladder muscle) with frequent urge to urinate, increased urination during the night, urgent urination, involuntary urination with or without the urge to urinate (incontinence), painful or difficult urination. Generally, although not necessarily, these disorders are caused by a neurogenic bladder. See, Guittard et al., U.S. Pat. No. 5,674,895, the content of which is incorporated herein by reference. In addition, oxybutynin may treat other conditions and disorders that are responsive to transdermal administration of oxybutynin, such as detrusor hyperreflexia and detrusor instability. Accordingly, in another aspect of the invention, a method is provided for the treatment of overactive bladder or urge and urinary incontinence in a subject, comprising administering to a subject in need thereof, a topical or transdermal composition of the present invention. Advantageously, the method of the invention provides a steady plasma concentration of oxybutynin to a subject administered with the composition as well as reduces peak plasma concentrations of oxybutynin and lowers a number of incidences and/or intensities of oxybutynin-associated side effects. Preferably, the method provides a sustained transdermal oxybutynin flux allowing therapeutic levels of oxybutynin for at least 24 hours. More preferably, the method provides a sustained transdermal oxybutynin flux allowing therapeutic levels of oxybutynin for at least 48 hours. Most preferably, the method provides a sustained transdermal oxybutynin flux allowing therapeutic levels of oxybutynin for at least 72 hours. Thus, the composition only needs to be administrated every once a day, every other day, every third day or twice per week.

EXAMPLES

The following examples are merely illustrative of the present invention and they should not be considered as limiting the scope of the invention in any way, as these examples and other equivalents thereof will become apparent to those skilled in the art in light of the present disclosure and the accompanying claims.

Example 1

A gel composed by oxybutynin free base 1 w/w to 5% w/w, anhydrous ethanol 45% w/w to 75% w/w, diethylene glycol monoethyl ether 1% w/w to 15% w/w, propylene glycol 1% w/w to 30% w/w, hydroxypropylcellulose (KLUCEL™ HF Pharm) 0.5% w/w to 2% w/w, hydrochloric acid HCl q. ad. for pH 4 to 9, and purified water q. ad. for 100% w/w, was prepared by dissolving the oxybutynin free base in the ethanol/propylene glycol/diethylene glycol monoethyl ether mixture. Purified water was then added and pH adjusted to the target with hydrochloric acid solution. Hydroxypropylcellulose was then thoroughly dispersed in the hydro-alcoholic solution under mechanical stirring at room temperature at a suitable speed ensuring good homogenization of the formulation while avoiding lumps formation and air entrapment until complete swelling.

Example 2

A gel composed by oxybutynin free base 3% w/w, anhydrous ethanol 50% w/w, diethylene glycol monoethyl ether 5% w/w, propylene glycol 15% w/w, hydroxypropylcellulose (KLUCEL™ HF Pharm) 1.5% w/w, hydrochloric acid HCl q. ad. for pH 7 to 8, and purified water q. ad. for 100% w/w, was prepared according to manufacturing process described in Example 1.

Example 3

A gel composed by oxybutynin free base 3% w/w, ethanol 96% w/w~55% w/w, diethylene glycol monoethyl ether 2.5% w/w, propylene glycol 20% w/w, hydroxypropylcellulose (KLUCEL™ HF Pharm) 1.5% w/w, butylhydroxytoluene (BHT) 0.05% w/w, hydrochloric acid HCl q. ad. for pH 7 to 8, and purified water q. ad. for 100% w/w, was prepared according to manufacturing process described in Example 1, wherein BHT is added to the ethanol/propylene glycol/diethylene glycol monoethyl ether mixture.

Example 4

Figure 2:
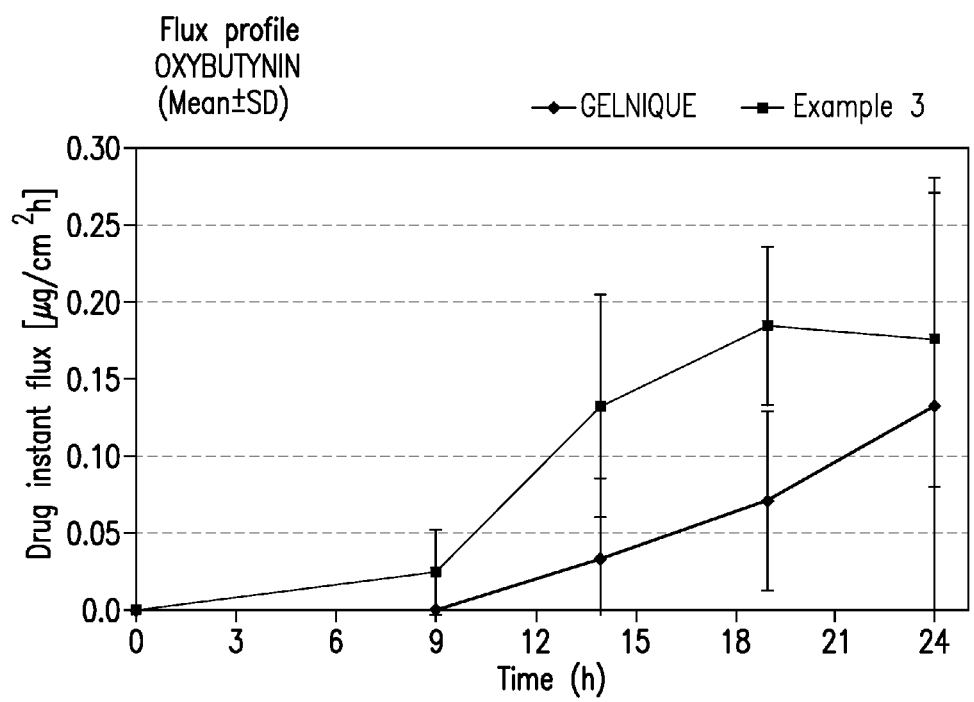
FIG. 2 is a graph illustrating the drug flux profiles of the compositions of FIG. 1.

In vitro study was conducted to determine the permeability profile of oxybutynin in human surgically excised skin using the oxybutynin formulation of Example 3 above, as compared with a marketed oxybutynin gel product (GELNIQUE®, Watson Laboratories, Inc.). Each formulation was tested in 6 replicates on frozen human skin (one single skin donor). Overall, twelve skin samples were used, which were processed and sliced prior to use. The thickness of each skin sample was measured with a micrometer. The skin samples were then mounted on vertical glass Franz diffusion cells with a receptor compartment of 7.39-7.78 mL, a donor compartment of 3 mL and a diffusion area of 1.77 $cm^2$. Phosphate buffered saline (PBS) at pH 7.4, with addition of 2% w/v oleyl ether of polyoxyethylene glycol (Brij® 98) was used as the receptor solution, and maintained at 35° C. during the whole study, under constant stirring (600 rpm). The study was performed by using a Microette® autosampler. After 2 hours pre-incubation of the skin samples with the receptor solution, and integrity assessment by evaporimetry (measurement of trans epidermal water loss, TEWL), about 10 mg (5.6 mg/$cm^2$) of the formulations were applied with the tip of a plastic syringe plunger and gently spread over the skin diffusion surface. Diffusion of the drug was allowed under non-occluded conditions during 24 hours. Receptor solution samples (1.2 mL) were automatically removed at 9-14-19-24 hours (after 0.8 mL receptor compartment priming). The samples were collected in 2 mL HPLC amber glass vials pre-sealed with septum crimp-caps previously filled with 10 µL of a solution of trifluoroacetic acid (TFA) 10%. Then samples were transferred into Eppendorf microtubes and centrifuged (14500 rpm during 10 min). Supernatant (0.9 mL) were then transferred in a 2 mL HPLC amber glass vial. Analysis of the samples was performed by appropriate HPLC method. The results of this study are presented in FIG. 1 and FIG. 2. At same drug loading, i.e. 5.8 mg gel/$cm^2$ skin, the formulation of Example 3 delivers significantly 2.3-fold more oxybutynin through the skin than GELNIQUE®, respectively 2.7 µg/$cm^2$ and 1.2 µg/$cm^2$ in 24 hours (p=0.02). Considering these in vitro data and assuming same pattern in vivo, we could conclude that application of 0.45 g of the formulation of Example 3 should be equivalent to application of 1 g of GELNIQUE®.

Example 5

A gel composed by oxybutynin free base 3% w/w, anhydrous ethanol 30% w/w, isopropanol 20% w/w, diethylene glycol monoethyl ether 2.5% w/w, propylene glycol 15% w/w, hydroxypropylcellulose (KLUCEL™ HF Pharm) 1.5% w/w, hydrochloric acid HCl q. ad. for pH 7 to 8, and purified water q. ad. for 100% w/w, was prepared according to manufacturing process described in Example 1 wherein isopropanol is added to the ethanol/propylene glycol/diethylene glycol monoethyl ether mixture.

Example 6

A gel composed by oxybutynin free base 3% w/w, anhydrous ethanol 30% w/w, isopropanol 20% w/w, diethylene glycol monoethyl ether 2.5% w/w, polyethylene glycol 600 10% w/w, hydroxypropylcellulose (KLUCEL™ MF Pharm) 1.5% w/w, hydrochloric acid HCl q. ad. for pH 6.5 to 7.5, and purified water q. ad. for 100% w/w, was prepared according to manufacturing process described in Example 1, wherein propylene glycol is substituted by polyethylene glycol 600.

Example 7

A gel composed by oxybutynin hydrochloride 10% w/w, anhydrous ethanol 60% w/w, diethylene glycol monoethyl ether 2.5% w/w, propylene glycol 2.5% w/w, hydroxypropylcellulose (KLUCEL™ MF Pharm) 2% w/w, butylhydroxytoluene (BHT) 0.05% w/w, sodium hydroxide NaOH q. ad. for pH 4 to 6, and purified water q. ad. for 100% w/w, was prepared by dissolving the oxybutynin hydrochloride in the ethanol/propylene glycol/diethylene glycol monoethyl ether/water mixture. pH was then adjusted to the target with sodium hydroxide solution. Hydroxypropylcellulose was then thoroughly dispersed in the hydro-alcoholic solution under mechanical stirring at room temperature at a suitable speed ensuring good homogenization of the formulation while avoiding lumps formation and air entrapment until complete swelling.

Example 8

A gel composed by oxybutynin hydrochloride 10% w/w, anhydrous ethanol 60% w/w, diethylene glycol monoethyl ether 5% w/w, propylene glycol 10% w/w, hydroxypropylcellulose (KLUCEL™ MF Pharm) 2% w/w, butylhydroxytoluene (BHT) 0.05% w/w, sodium hydroxide NaOH q. ad. for pH 4 to 6, and purified water q. ad. for 100% w/w, was prepared according to manufacturing process described in Example 7.

Example 9

Figure 3:
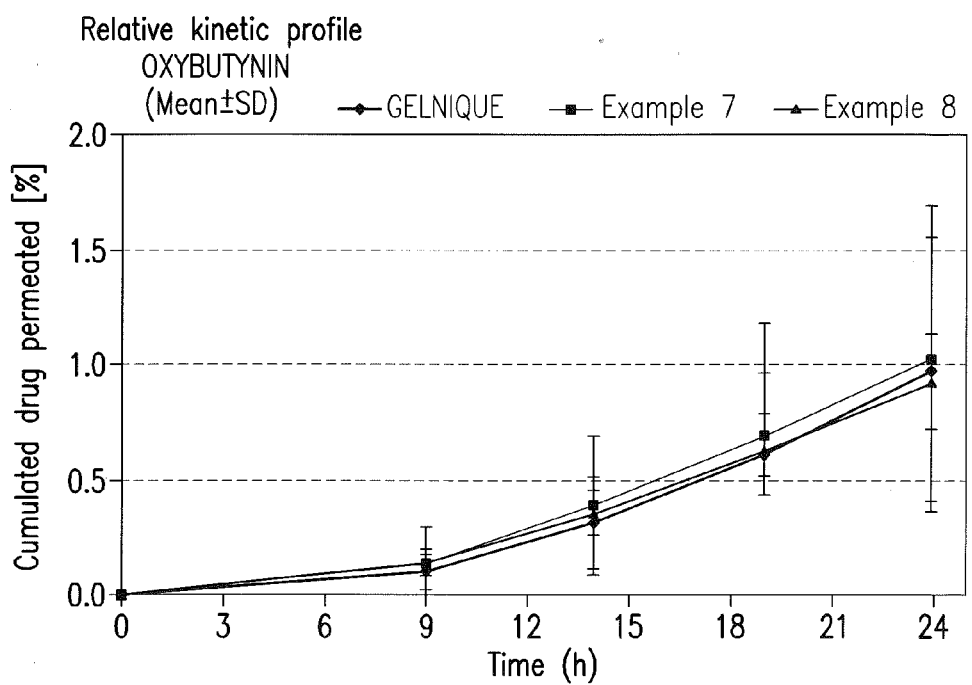
FIG. 3 is a graph illustrating the results from an in-vitro 24-hour comparative permeation study comparing permeation of two compositions comprising oxybutynin of the present invention, and a marketed product.
Figure 4:
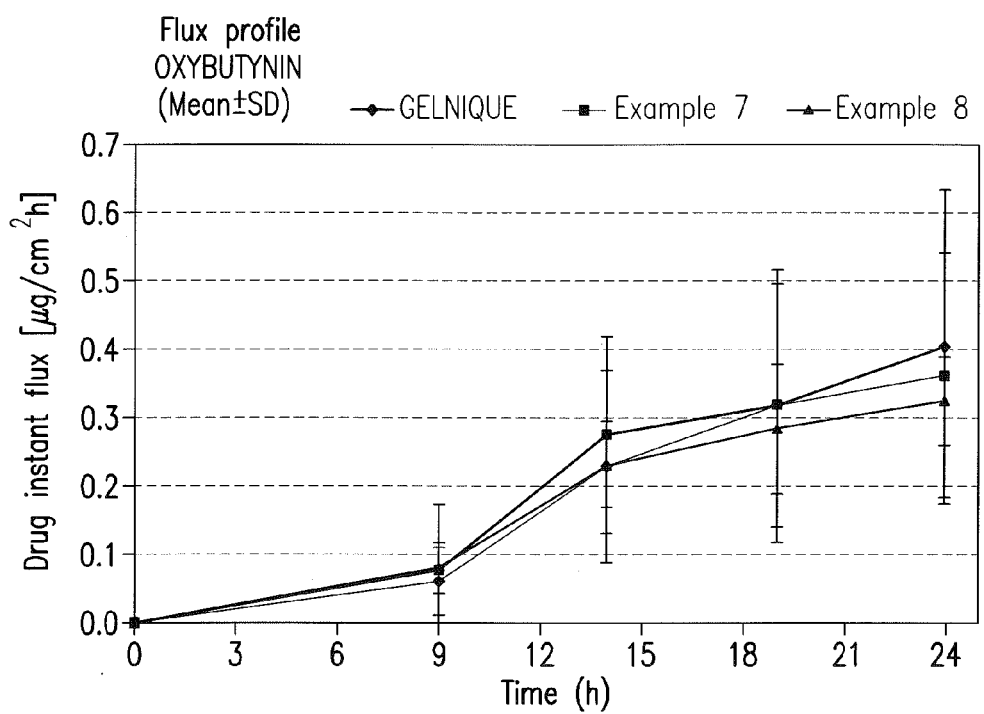
FIG. 4 is a graph illustrating the drug flux profiles of the compositions of FIG. 3.

In vitro study was conducted to determine the permeability profile of oxybutynin in pig ear skin using the oxybutynin formulations of Example 7 and Example 8 above, as compared with a marketed oxybutynin gel product (GELNIQUE®, Watson Laboratories, Inc.). Each formulation was tested in 4 replicates (4 donors randomly assigned so that each formulation is tested once on each skin sample). Procedure is the same as those described above in Example 4. The results of this study are presented in FIG. 3 and FIG. 4. At same drug loading, i.e. about 5.8 mg gel/cm$^2$ skin, the two formulations of Example 7 and Example 8 are equivalent to GELNIQUE®.

Example 10

A gel composed by oxybutynin hydrochloride 10% w/w, anhydrous ethanol 60% w/w, diethylene glycol monoethyl ether 5 w/w, propylene glycol 5% w/w, hydroxypropylcellulose (KLUCEL™ MF Pharm) 2% w/w, butylhydroxytoluene (BHT) 0.05% w/w, sodium hydroxide NaOH q. ad. for pH 4 to 6, and purified water q. ad. for 100% w/w, was prepared according to manufacturing process described in Example 7.

Example 11

A gel composed by oxybutynin hydrochloride 10% w/w, anhydrous ethanol 60% w/w, diethylene glycol monoethyl ether 1% w/w, propylene glycol 1% w/w, hydroxypropylcellulose (KLUCEL™ MF Pharm) 2% w/w, butylhydroxytoluene (BHT) 0.05% w/w, sodium hydroxide NaOH q. ad. for pH 4 to 6, and purified water q. ad. for 100% w/w, was prepared according to manufacturing process described in Example 7.

Example 12

A gel composed by oxybutynin hydrochloride 10% w/w, anhydrous ethanol 60% w/w, diethylene glycol monoethyl ether 5% w/w, propylene glycol 2.5% w/w, hydroxypropylcellulose (KLUCEL™ MF Pharm) 2.00% w/w, butylhydroxytoluene (BHT) 0.05% w/w, sodium hydroxide NaOH q. ad. for pH 4 to 6, and purified water q. ad. for 100% w/w, was prepared according to manufacturing process described in Example 7.

Example 13

Comparative

A gel composed by oxybutynin hydrochloride 10% w/w, anhydrous ethanol 60% w/w, diethylene glycol monoethyl ether 5% w/w, propylene glycol 6% w/w, tetradecanol (myristyl alcohol) 1% w/w, hydroxypropylcellulose (KLUCEL™ MF Pharm) 1.5 w/w, butylhydroxytoluene (BHT) 0.05% w/w, sodium hydroxide NaOH q. ad. for pH 4 to 6, and purified water q. ad. for 100% w/w, was prepared according to manufacturing process described in Example 7.

Example 14

Comparative

A gel composed by oxybutynin hydrochloride 10% w/w, anhydrous ethanol 60% w/w, diethylene glycol monoethyl ether 5% w/w, propylene glycol 6% w/w, dodecanol (lauryl alcohol) 1% w/w, hydroxypropylcellulose (KLUCEL™ MF Pharm) 1.5% w/w, butylhydroxytoluene (BHT) 0.05% w/w, sodium hydroxide NaOH q. ad. for pH 4 to 6, and purified water q. ad. for 100% w/w, was prepared according to manufacturing process described in Example 7.

Example 15

Figure 5:
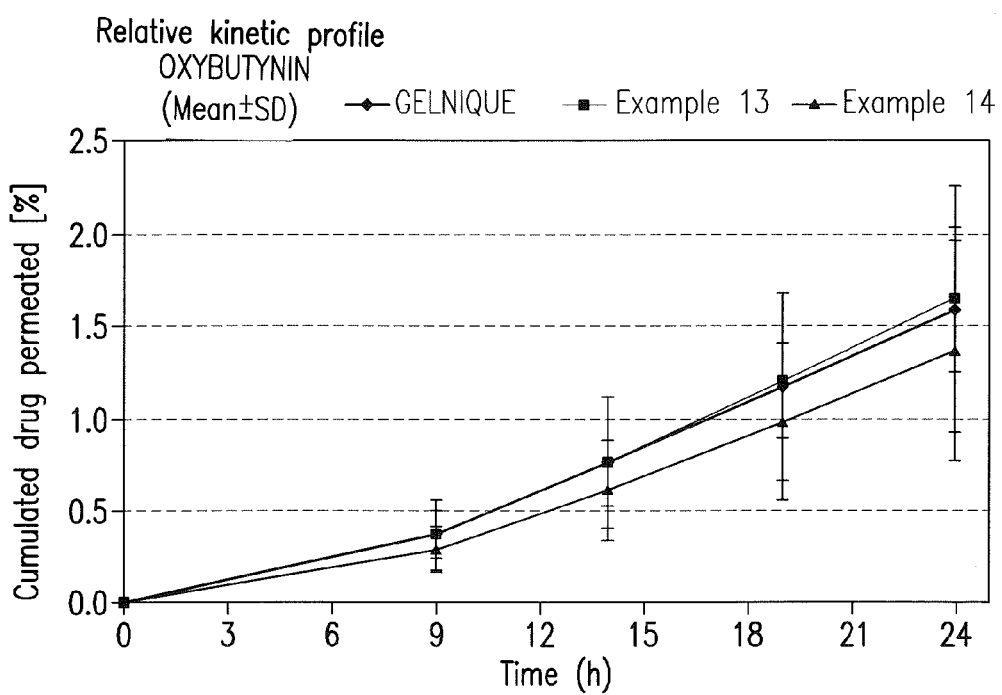
FIG. 5 is a graph illustrating the results from an in-vitro 24-hour comparative permeation study comparing permeation of two compositions comprising oxybutynin out of the scope of the present invention, and a marketed product.
Figure 6:
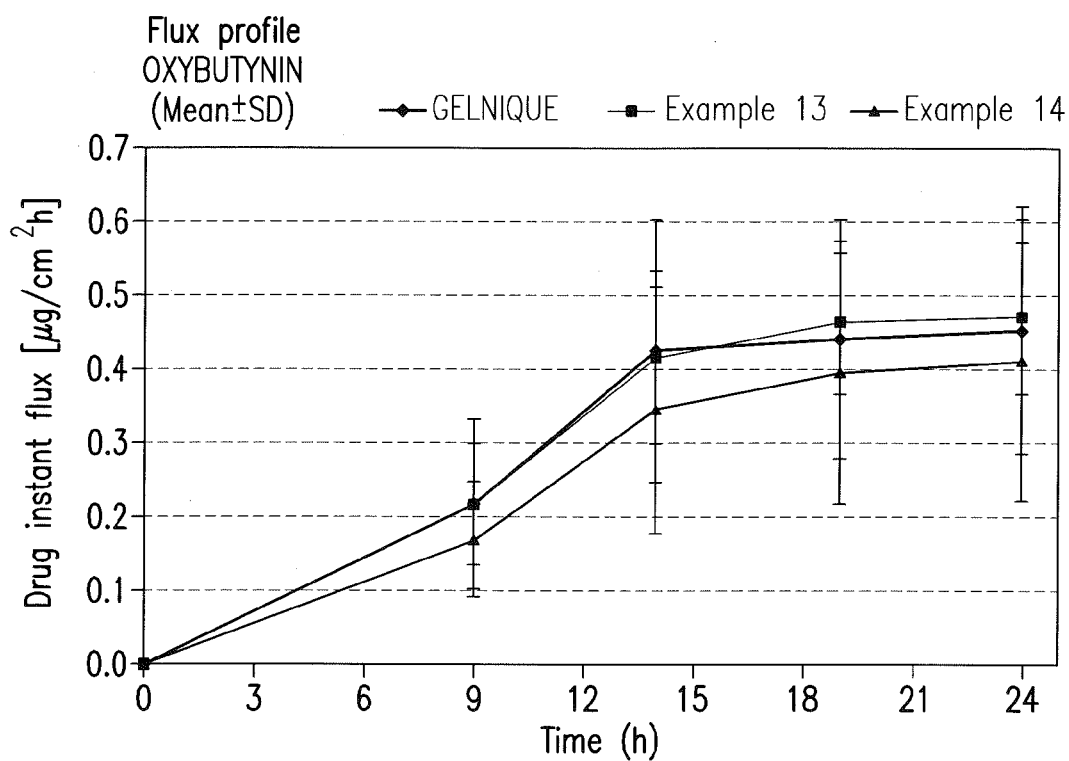
FIG. 6 is a graph illustrating the drug flux profiles of the compositions of FIG. 5.

In vitro study was conducted to determine the permeability profile of oxybutynin in pig ear skin using the oxybutynin formulations of Example 13 and Example 14 above, as compared with a marketed oxybutynin gel product (GELNIQUE®, Watson Laboratories, Inc.). Each formulation was tested in 4 replicates. Procedure is the same as those described above in Example 9. The results of this study are presented in FIG. 5 and FIG. 6. At same drug loading, i.e. about 5.8 mg gel/cm$^2$ skin, the two formulations of Example 13 and Example 14 are equivalent to GELNIQUE®. Therefore addition of long-chain fatty alcohols to a composition of the present invention neither improves nor impairs the skin penetration of oxybutynin.

Example 16

A gel composed by oxybutynin free base 3% w/w, anhydrous ethanol 58.1% w/w, diethylene glycol monoethyl ether 5% w/w, propylene glycol 6% w/w, hydroxypropylcellulose (KLUCEL™ HF Pharm) 2.00% w/w, hydrochloric acid HCl q. ad. for pH 7 to 7.5, and purified water q. ad. for 100% w/w, was prepared according to manufacturing process described in Example 1.

Example 17

Comparative

A gel composed by oxybutynin free base 3% w/w, anhydrous ethanol 58.1% w/w, diethylene glycol monoethyl ether 5% w/w, propylene glycol 6% w/w, dodecanol (lauryl alcohol) 1%, hydroxypropylcellulose (KLUCEL™ HF Pharm) 2% w/w, hydrochloric acid HCl q. ad. for pH 7 to 7.5, and purified water q. ad. for 100% w/w, was prepared according to manufacturing process described in Example 1.

Example 18

Comparative

A gel composed by oxybutynin free base 3% w/w, anhydrous ethanol 58.1% w/w, diethylene glycol monoethyl ether 5% w/w, propylene glycol 6% w/w, oleyl alcohol 1%, hydroxypropylcellulose (KLUCEL™ HF Pharm) 2% w/w, hydrochloric acid HCl q. ad. for pH 7 to 7.5, and purified water q.

ad. for 100% w/w, was prepared according to manufacturing process described in Example 1.

Example 19

Figure 7:
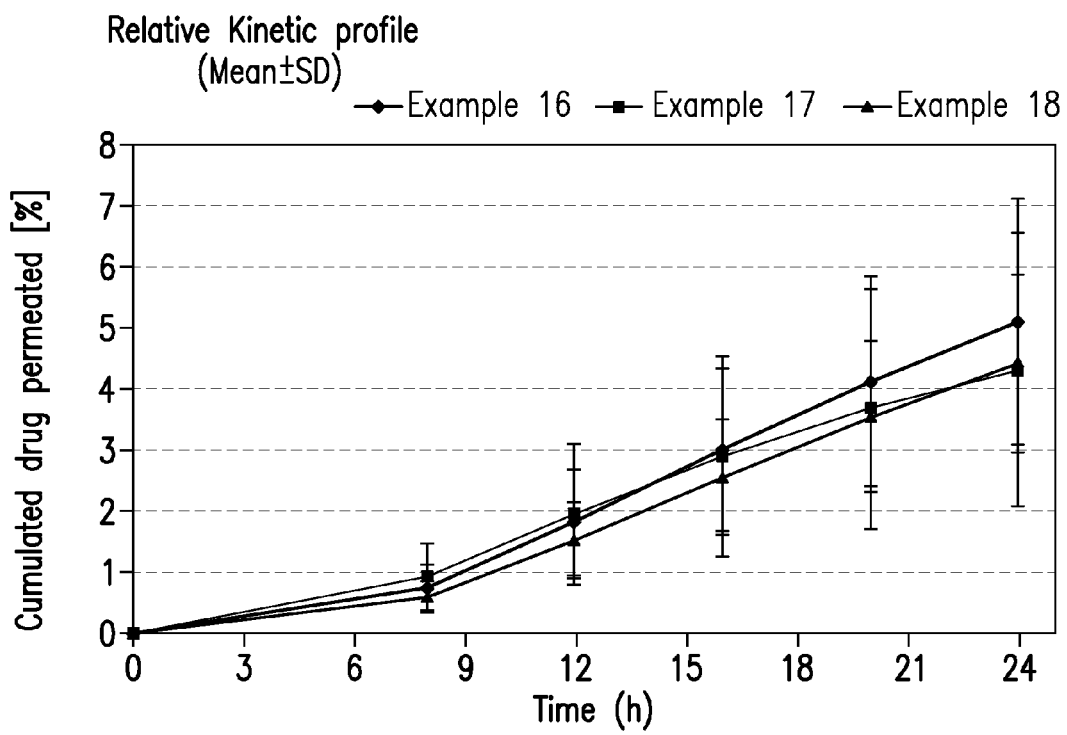
FIG. 7 is a graph illustrating the results from an in-vitro 24-hour comparative permeation study comparing permeation of a composition comprising oxybutynin of the present invention, and two compositions comprising oxybutynin out of the scope of the present invention.
Figure 8:
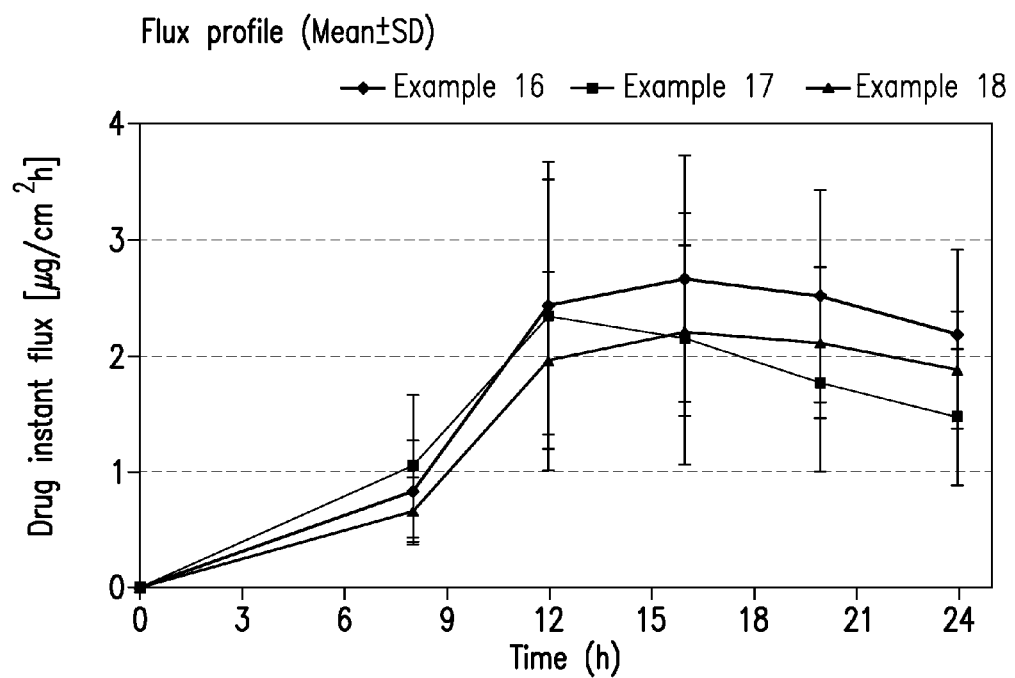
FIG. 8 is a graph illustrating the drug flux profiles of the compositions of FIG. 7.

In vitro study was conducted to determine the permeability profile of oxybutynin in pig ear skin using the oxybutynin formulations out of the scope of the present invention of Example 17 and Example 18 above, as compared with oxybutynin formulation of the present invention of Example 16. Each formulation was tested in 4 replicates. Procedure is the same as those described above in Example 9 except that about 50 mg of formulations were applied on each skin sample. The results of this study are presented in FIG. 7 and FIG. 8. At same drug loading, i.e. about 30 mg gel/cm$^2$ skin, the two formulations of Example 16 and Example 17 are equivalent to the formulations of Example 16. Therefore addition of long-chain fatty alcohols to a composition of the present invention neither improves nor impairs the skin penetration of oxybutynin.

Example 20

A gel composed by oxybutynin free base 5% w/w, anhydrous ethanol 51.66% w/w, diethylene glycol monoethyl ether 5% w/w, propylene glycol 6% w/w, hydroxypropylcellulose (KLUCEL™ HF Pharm) 2% w/w, hydrochloric acid HCl q. ad. for pH 7 to 7.5, and purified water q. ad. for 100% w/w, was prepared according to manufacturing process described in Example 1.

Example 21

Comparative

A gel composed by oxybutynin free base 5% w/w, anhydrous ethanol 51.66% w/w, diethylene glycol monoethyl ether 5% w/w, propylene glycol 6% w/w, glycerol monolaurate 5% w/w, hydroxypropylcellulose (KLUCEL™ HF Pharm) 2% w/w, hydrochloric acid HCl q. ad. for pH 7 to 7.5, and purified water q. ad. for 100% w/w, was prepared according to manufacturing process described in Example 1.

Example 22

Comparative

A gel composed by oxybutynin free base 5% w/w, anhydrous ethanol 51.66% w/w, diethylene glycol monoethyl ether 5% w/w, propylene glycol 6% w/w, propylene glycol monolaurate 5% w/w, hydroxypropylcellulose (KLUCEL™ HF Pharm) 2% w/w, hydrochloric acid HCl q. ad. for pH 7 to 7.5, and purified water q. ad. for 100% w/w, was prepared according to manufacturing process described in Example 1.

Example 23

Figure 9:
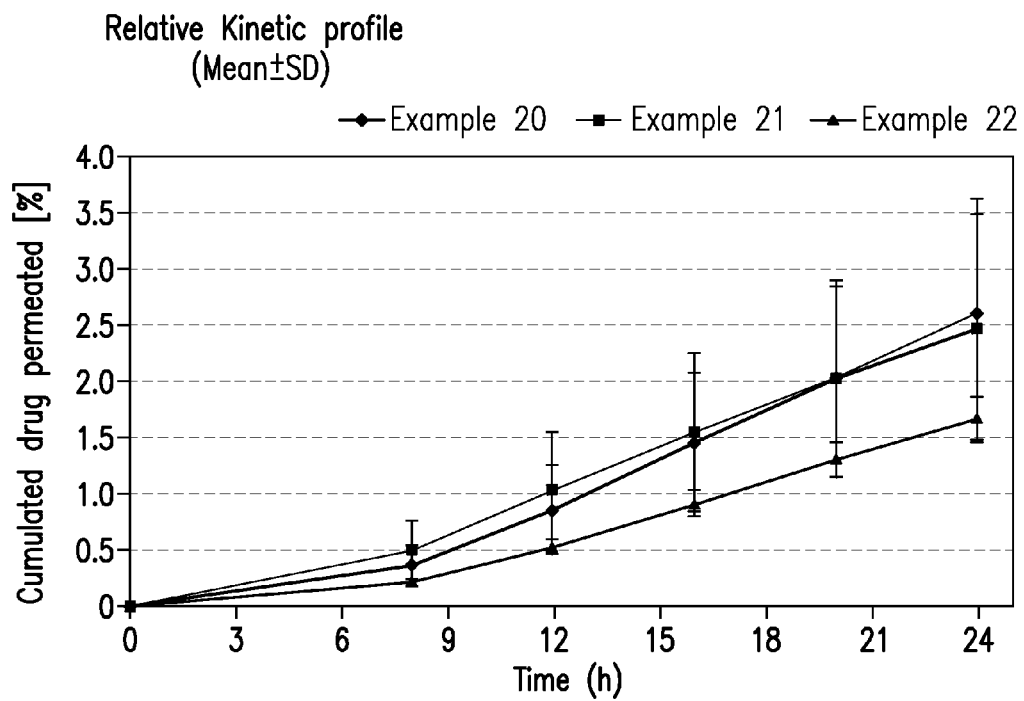
FIG. 9 is a graph illustrating the results from an in-vitro 24-hour comparative permeation study comparing permeation of a composition comprising oxybutynin of the present invention, and two compositions comprising oxybutynin out of the scope of the present invention.
Figure 10:
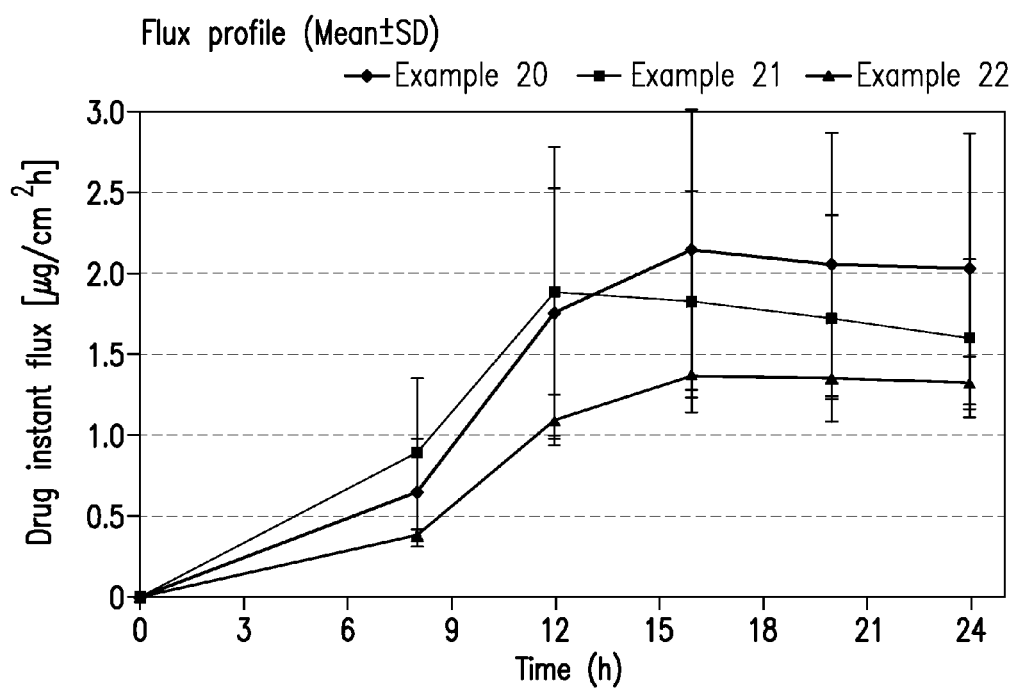
FIG. 10 is a graph illustrating the drug flux profiles of the compositions of FIG. 9.

In vitro study was conducted to determine the permeability profile of oxybutynin in pig ear skin using the oxybutynin formulations out of the scope of the present invention of Example 21 and Example 22 above, as compared with oxybutynin formulation of the present invention of Example 20. Each formulation was tested in 4 replicates. Procedure is the same as those described above in Example 19. The results of this study are presented in FIG. 9 and FIG. 10. At same drug loading, i.e. about 30 mg gel/cm$^2$ skin, the two comparative formulations of Example 20 and Example 21 are equivalent to the formulations of Example 20. Therefore addition of long-chain fatty esters to a composition of the present invention does not improve the skin penetration of oxybutynin.

Example 24

Comparative

A gel composed by oxybutynin free base 3% w/w, anhydrous ethanol 58.1% w/w, diethylene glycol monoethyl ether 5% w/w, propylene glycol 6% w/w, lauric acid 1%, hydroxypropylcellulose (KLUCEL™ HF Pharm) 2% w/w, hydrochloric acid HCl q. ad. for pH 7 to 7.5, and purified water q. ad. for 100% w/w, was prepared according to manufacturing process described in Example 1.

Example 25

Figure 11:
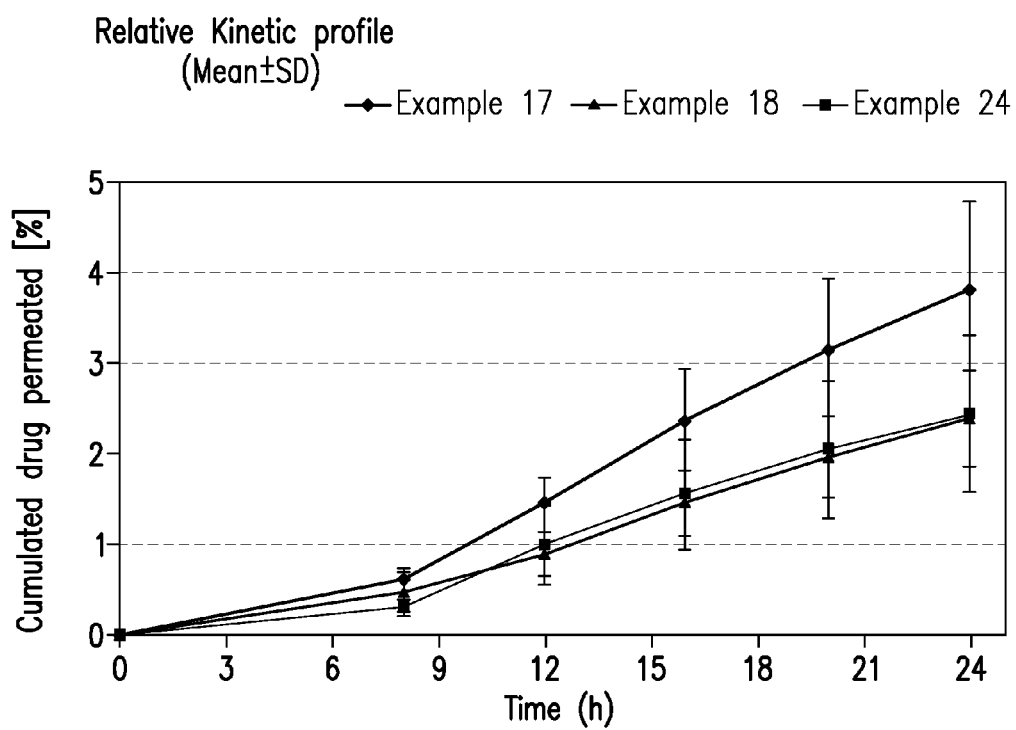
FIG. 11 is a graph illustrating the results from an in-vitro 24-hour comparative permeation study comparing permeation of three compositions comprising oxybutynin out of the scope of the present invention.
Figure 12:
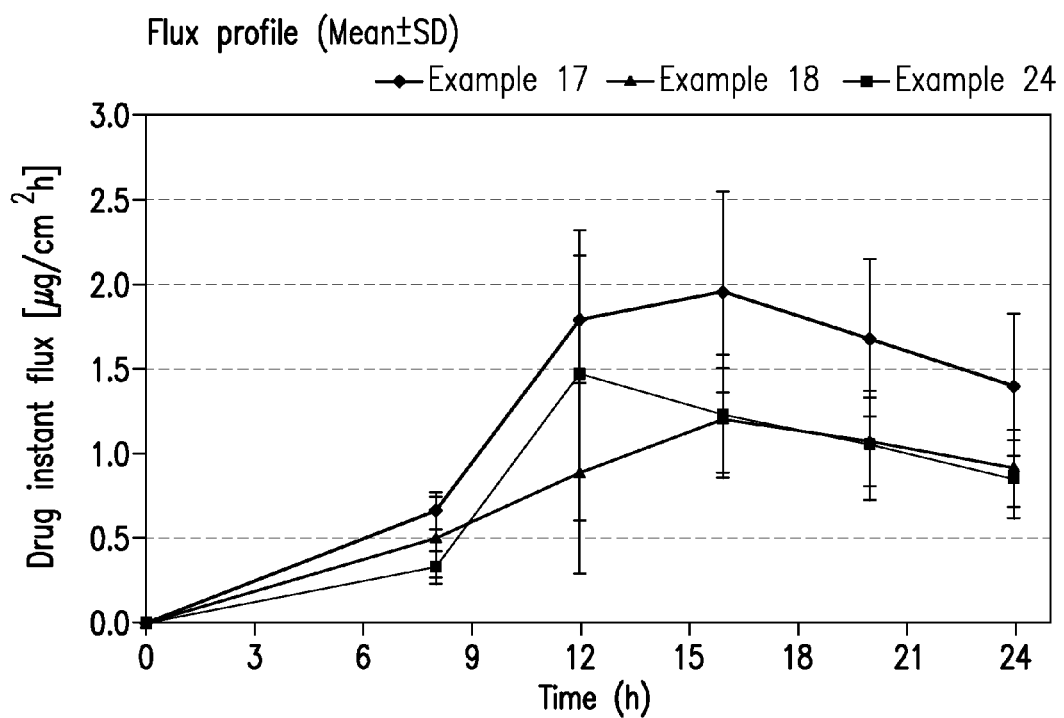
FIG. 12 is a graph illustrating the drug flux profiles of the compositions of FIG. 11.

In vitro study was conducted to determine the permeability profile of oxybutynin in pig ear skin using the oxybutynin formulations out of the scope of the present invention of Example 17, Example 18 and Example 24 above. Each formulation was tested in 4 replicates. Procedure is the same as those described above in Example 19. The results of this study are presented in FIG. 11 and FIG. 12. At same drug loading, i.e. about 30 mg gel/cm$^2$ skin, the three formulations of Example 17, Example 18 and comparative Example 24 are equivalent to the formulations of Example 20. Therefore addition of long-chain fatty acids to a composition of the present invention does not improve the skin penetration of oxybutynin.

Example 26

Pilot Pharmacokinetic Study of an Oxybutynin Gel Formulation of the Present Invention in Healthy Volunteers In vivo study was conducted by a qualified investigator to determine the pharmacokinetics of oxybutynin in healthy human volunteers. The study was a single-center, multiple-dose, open-label study during which the oxybutynin formulation of the present invention of Example 3 above was tested. This study was planned and performed in accordance with the Declaration of Helsinki in its version of Somerset West, 1996, and in accordance with the EU Clinical Trial Directive 2001/20/EC and relevant guidances ("Note for Guidance on Good Clinical Practice", CPMP/ICH/135/95 of Jan. 17, 1997; "Note for Guidance on the Investigation of Bioavailability and Bioequivalence", CPMP/EWP/QWP/1401/98; "Note for Guidance on modified release oral and transdermal dosage forms: Section II", CPMP/EWP/280/96). Treatment consisted in multiple doses of 2.8 g of gel per day (corresponding to 84 mg oxybutynin per day) administered each morning for 7 consecutive days. The gel was distributed over a skin area of 700 cm$^2$ on the abdomen.

58 non-smoking males and females (including 25-40 women), aged 18 to 55, white, physically and mentally healthy as confirmed by an interview, medical history, clinical examination and having given written informed consent, enrolled in this study. Summary data on study population are presented in Table 5 herein. 54 subjects completed the study. Blood sampling was performed on Day 1 at initiation of the study (H0), and then on Day 7 (H0+144; H0+146; H0+148; H0+152; H0+156), Day 8 (H0+160; H0+164; H0+168), Day 9 (H0+192), Day 10 (H0+216), Day 11 (H0+240) and Day 12 (H0+264). Blood samples were then processed and analyzed by LC-MS-MS method (LLOQ set to 50 ng/ml). Criteria considered for evaluation were Pharmacokinetics (oxybutynin and N-desethyloxybutynin), area under the concentration-time curve ($AUC_T$), highest concentration determined in the measuring interval ($C_{max}$), and adverse events and vital signs. Summary results of this study are presented in Table 6 and in Table 7 herein.

TABLE 5

Pilot pharmacokinetic study of an oxybutynin gel formulation of the present invention in healthy volunteers: demographic data, safety population

| Sex | Ethnic origin | Stat. | Age [years] | Body weight [kg] | Height [cm] | BMI [kg/m²] |
|---|---|---|---|---|---|---|
| female and male | white, N = 58 | N | 58 | 58 | 58 | 58 |
| | | Mean | 36.1 | 72.9 | 174.8 | 23.74 |
| | | SD | 8.3 | 11.9 | 9.2 | 2.38 |
| | | CV | 23.1 | 16.3 | 5.3 | 10.02 |
| | | Minimum | 22 | 48 | 156 | 19.2 |
| | | Median | 34.0 | 74.0 | 176.0 | 24.15 |
| | | Maximum | 52 | 100 | 199 | 27.0 |
| female, N = 32 | white, N = 32 | N | 32 | 32 | 32 | 32 |
| | | Mean | 34.5 | 65.4 | 168.5 | 22.99 |
| | | SD | 8.9 | 9.2 | 6.2 | 2.54 |
| | | CV | 25.9 | 14.1 | 3.7 | 11.04 |
| | | Minimum | 22 | 48 | 156 | 19.2 |
| | | Median | 31.0 | 63.0 | 168.0 | 22.20 |
| | | Maximum | 51 | 92 | 185 | 27.0 |
| males N = 26 | white, N = 26 | N | 26 | 26 | 26 | 26 |
| | | Mean | 38.2 | 82.2 | 182.5 | 24.67 |
| | | SD | 7.2 | 7.5 | 5.7 | 1.82 |
| | | CV | 18.9 | 9.1 | 3.1 | 7.36 |
| | | Minimum | 27 | 66 | 176 | 20.6 |
| | | Median | 37.0 | 83.0 | 181.5 | 25.20 |
| | | Maximum | 52 | 100 | 199 | 26.9 |

TABLE 6

Pilot pharmacokinetic study of an oxybutynin gel formulation of the present invention in healthy volunteers: summary kinetic variables for oxybutynin

| Variable | Statistics | Results |
|---|---|---|
| $AUC_T$ [ng/ml * h] | N | 54 |
| | Mean | 156.0676 |
| | SD | 62.7989 |
| | GeoM | 143.6709 |
| | G_CV | 44.4 |
| $C_{av}$ [ng/ml] | N | 54 |
| | Mean | 6.5028 |
| | SD | 2.6166 |
| | GeoM | 5.9863 |
| | G_CV | 44.4 |
| $C_{max}$ [ng/ml] | N | 54 |
| | Mean | 9.7444 |
| | SD | 5.1062 |
| | GeoM | 8.6067 |
| | G_CV | 54.7 |
| $C_{min}$ [ng/ml] | N | 54 |
| | Mean | 4.3767 |
| | SD | 1.8940 |
| | GeoM | 4.0096 |
| | G_CV | 44.5 |
| PTF | N | 54 |
| | Mean | 0.77 |
| | SD | 0.31 |
| | GeoM | 0.71 |
| | G_CV | 41.7 |
| R (coefficient of correlation) | N | 54 |
| | Min | −1.000 |
| | Med | −0.994 |
| | Max | −0.863 |

TABLE 6-continued

Pilot pharmacokinetic study of an oxybutynin gel formulation of the present invention in healthy volunteers: summary kinetic variables for oxybutynin

| Variable | Statistics | Results |
|---|---|---|
| $t_{1/2}$ [h] | N | 54 |
| | Mean | 29.18 |
| | SD | 8.35 |
| | GeoM | 28.16 |
| | G_CV | 26.7 |
| $t_{max}$ [h] | N | 54 |
| | Mean | 6.67 |
| | SD | 6.20 |
| | CV | 93.0 |
| | Min | 0.00 |
| | Med | 4.00 |
| | Max | 24.00 |
| $T_{cav}$ [h] | N | 54 |
| | Mean | 10.42 |
| | SD | 1.69 |
| | CV | 16.2 |
| | Min | 7.24 |
| | Med | 10.27 |
| | Max | 15.05 |

AUC: area under the concentration time curve;
$C_{AV}$: average steady state concentration;
$C_{max}$: highest concentration determined in the measuring interval;
$C_{min}$: lowest concentration determined in the measuring interval;
PTF: peak trough fluctuation;
$t_{1/2}$: half-life;
$t_{max}$: time at which Cmax occurs;
$T_{Cav}$: time period of concentration being above Cav;
N: number of subjects;
SD: standard deviation;
GeoM: geometric mean;
G_CV: geometric coefficient of variance (%) of geometric mean.

TABLE 7

Pilot pharmacokinetic study of an oxybutynin gel formulation of the present invention in healthy volunteers: summary kinetic variables for N-Desethyloxybutynin

| Variable | Statistics | Results |
|---|---|---|
| $AUC_T$ [ng/ml * h] | N | 54 |
| | Mean | 157.7218 |
| | SD | 88.6001 |
| | GeoM | 137.7699 |
| | G_CV | 55.3 |
| $C_{av}$ [ng/ml] | N | 54 |
| | Mean | 6.5717 |
| | SD | 3.6917 |
| | GeoM | 5.7404 |
| | G_CV | 55.3 |
| $C_{max}$ [ng/ml] | N | 54 |
| | Mean | 8.9495 |
| | SD | 5.3402 |
| | GeoM | 7.6858 |
| | G_CV | 59.2 |
| $C_{min}$ [ng/ml] | N | 54 |
| | Mean | 4.6255 |
| | SD | 2.6520 |
| | GeoM | 4.0281 |
| | G_CV | 56.0 |
| PTF | N | 54 |
| | Mean | 0.64 |
| | SD | 0.23 |
| | GeoM | 0.59 |
| | G_CV | 40.3 |
| R (coefficient of correlation) | N | 54 |
| | Min | −1.000 |
| | Med | −0.996 |
| | Max | −0.872 |

TABLE 7-continued

Pilot pharmacokinetic study of an oxybutynin gel formulation of the present invention in healthy volunteers: summary kinetic variables for N-Desethyloxybutynin

| Variable | Statistics | Results |
|---|---|---|
| $t_{1/2}$ [h] | N | 54 |
| | Mean | 31.17 |
| | SD | 8.42 |
| | GeoM | 30.11 |
| | G_CV | 27.0 |
| $t_{max}$ [h] | N | 54 |
| | Mean | 7.97 |
| | SD | 4.44 |
| | Min | 0.00 |
| | Med | 8.00 |
| | Max | 24.00 |
| $T_{Cav}$ [h] | N | 54 |
| | Mean | 10.79 |
| | SD | 1.55 |
| | Min | 6.96 |
| | Med | 10.63 |
| | Max | 13.61 |

AUC: area under the concentration time curve;
$C_{AV}$: average steady state concentration
$C_{max}$: highest concentration determined in the measuring interval;
$C_{min}$: lowest concentration determined in the measuring interval;
PTF: peak trough fluctuation;
$t_{1/2}$: half-life;
$t_{max}$: time at which Cmax occurs;
$T_{Cav}$: time period of concentration being above Cav;
N: number of subjects;
SD: standard deviation;
GeoM: geometric mean;
G_CV: geometric coefficient of variance (%) of geometric mean.

TABLE 8

Pilot pharmacokinetic study of an oxybutynin gel formulation of the present invention in healthy volunteers: number and percent of subjects (N = 56) reporting adverse events occurring after 1st administration

| Total number (%) of subjects with AE | 28 (50%) |
|---|---|
| Cardiac disorders | 0 (0%) |
| Tachycardia | 0 (0%) |
| Eye disorders | 3 (5%) |
| Vision blurred | 2 (4%) |
| Dry eye | 1 (2%) |
| Eye irritation | 0 (0%) |
| Gastrointestinal disorders | 10 (18%) |
| Dry mouth | 7 (13%) |
| Nausea | 3 (5%) |
| Flatulence | 2 (4%) |
| Abdominal distension | 1 (2%) |
| Vomiting | 1 (2%) |
| Abdominal pain | 0 (0%) |
| Abdominal pain upper | 1 (2%) |
| Constipation | 1 (2%) |
| General disorders and administration site conditions | 8 (14%) |
| Fatigue | 2 (4%) |
| Application site erythema | 1 (2%) |
| Application site pruritus | 1 (2%) |
| Application site anaesthesia | 0 (0%) |
| Application site cold feeling | 1 (2%) |
| Application site exfoliation | 0 (0%) |
| Application site irritation | 1 (2%) |
| Asthenia | 1 (2%) |
| Non-cardiac chest pain | 1 (2%) |
| Pyrexia | 1 (2%) |
| Infections and infestations | 4 (7%) |
| Nasopharyngitis | 4 (7%) |
| Cystitis | 0 (0%) |
| Gastroenteritis | 0 (0%) |
| Urinary tract infection | 0 (0%) |
| Injury, poisoning and procedural complications | 1 (2%) |
| Skin laceration | 0 (0%) |

TABLE 8-continued

Pilot pharmacokinetic study of an oxybutynin gel formulation of the present invention in healthy volunteers: number and percent of subjects (N = 56) reporting adverse events occurring after 1st administration

| Vessel puncture site paraesthesia | 1 (2%) |
|---|---|
| Metabolism and nutrition disorders | 2 (4%) |
| Anorexia | 2 (4%) |
| Musculoskeletal and connective tissue disorders | 0 (0%) |
| Myotonia | 0 (0%) |
| Nervous system disorders | 12 (21%) |
| Headache | 11 (20%) |
| Dizziness | 1 (2%) |
| Post-traumatic headache | 0 (0%) |
| Renal and urinary disorders | 1 (2%) |
| Micturition urgency | 0 (0%) |
| Pollakiuria | 1 (2%) |
| Reproductive system and breast disorders | 1 (2%) |
| Breast pain | 0 (0%) |
| Menstrual disorder | 0 (0%) |
| Metrorrhagia | 1 (2%) |
| Respiratory, thoracic and mediastinal disorders | 2 (4%) |
| Oropharyngeal pain | 2 (4%) |

Figure 13:
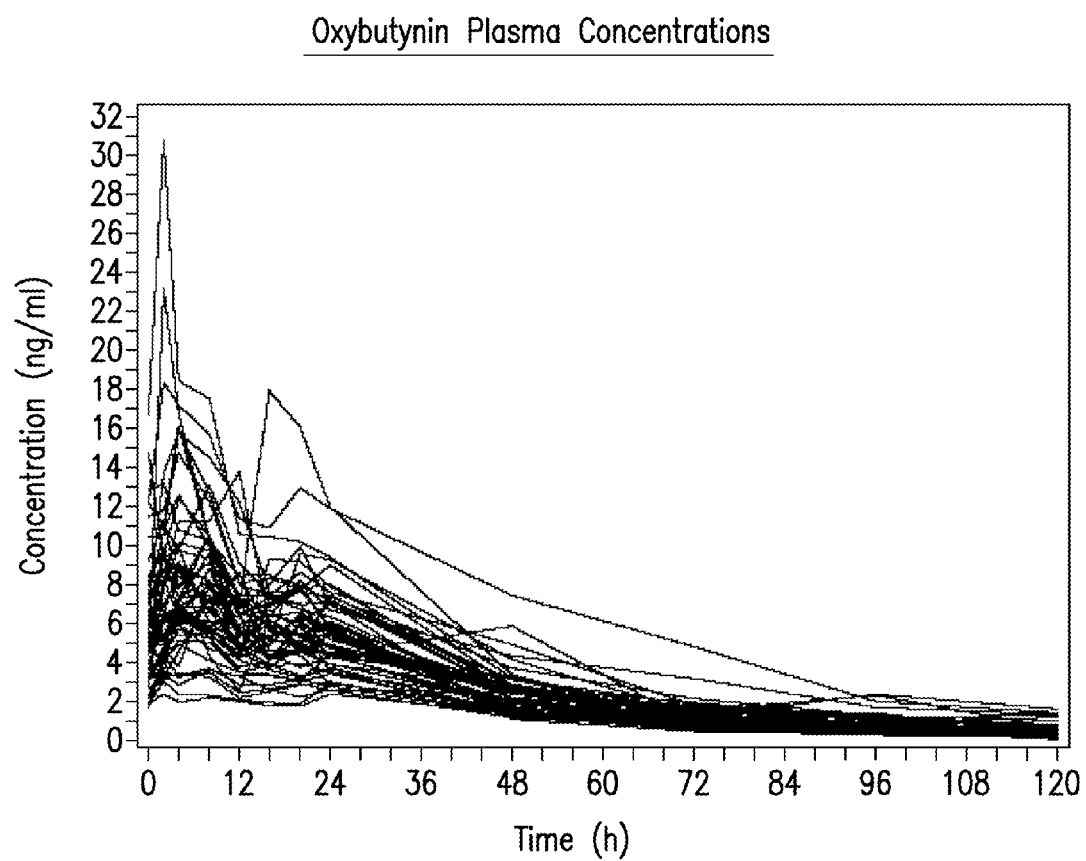
FIG. 13 is a graph illustrating the plasmatic concentrations of oxybutynin in healthy volunteers during the pilot pharmacokinetic study of an oxybutynin gel formulation of the present invention.

Plasmatic oxybutynin concentration reached a steady state after 6 repeated doses. The average plasmatic concentration of oxybutynin was 5.99 ng/ml. $C_{max}$ was 8.61 ng/ml (geometric mean). $T_{max}$, the time at which the concentration of oxybutynin ($C_{max}$) peaks, occurred about 4 hours (median) after application. The terminal half-life $T_{1/2}$ was 28.16 hours (geometric mean). See FIG. 13.

Figure 14:
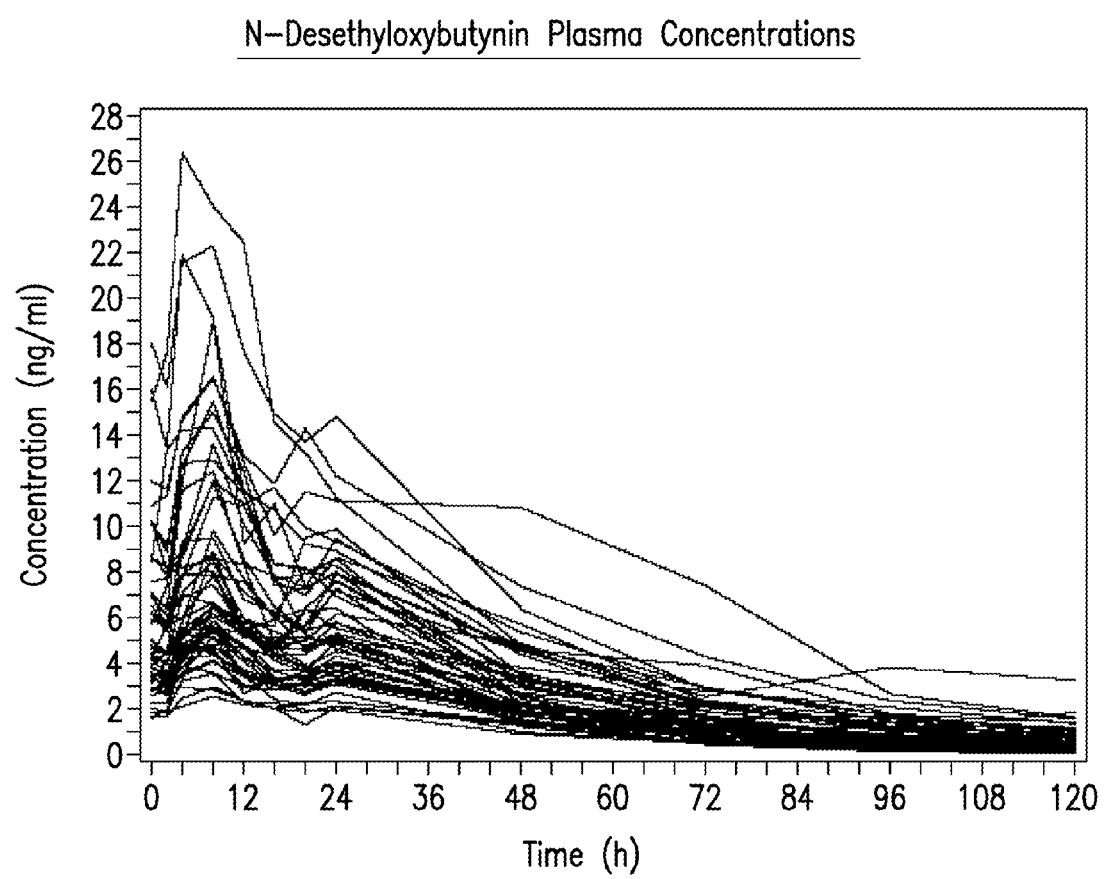
FIG. 14 is a graph illustrating the plasmatic concentrations of N-desethyloxybutynin in healthy volunteers during the pilot pharmacokinetic study of an oxybutynin gel formulation of the present invention.

Plasmatic N-desethyloxybutynin concentration reached also steady state after 6 repeated doses. The average plasmatic concentration of oxybutynin was 5.74 ng/ml. $C_{max}$ was 7.69 ng/ml (geometric mean). $T_{max}$, the time at which the concentration of oxybutynin ($C_{max}$) peaks, occurred about 8 hours (median) after application. The terminal half-life $T_{1/2}$ was 30.11 hours (geometric mean). See FIG. 14.

The majority of the reported adverse events (AEs) was classified as related to the study medication itself. The most often observed AE was dry mouth (13% of subjects), reported as a common side-effect of oxybutynin. The other common side-effects were reported infrequently (5% of subjects or less). The observed skin-tolerability of the treatment was good, with only eight subjects reporting mild skin reactions. No significant changes in vital signs, electrocardiogram parameters, physical findings or in clinical laboratory variables were detected. The results are shown in Table 8 herein.

While the invention has been described and pointed out in detail with reference to operative embodiments thereof, it will be understood by those skilled in the art that various changes, modifications, substitutions, and omissions can be made without departing from the spirit of the invention. It is intended therefore, that the invention embrace those equivalents within the scope of the claims that follow.

What is claimed is:

1. A composition for transdermal or transmucosal administration of oxybutynin consisting essentially of:
   oxybutynin in an amount between 1 to 3% by weight of the composition;
   a delivery vehicle which consists essentially of a C2 to C4 alkanol present in an amount of 45 to no more than 65% by weight of the composition, a polyalcohol selected from the group consisting of propylene glycol, dipropylene glycol, polyethylene glycol, glycerin, and mixtures thereof in an amount greater than 15 to about 30% by weight of the composition, a monoalkyl ether of diethylene glycol in an amount between about 1 to 5% by weight of the composition, and water, so that the delivery vehicle provides permeation enhancement of oxybutynin through mammalian dermal or mucosal surfaces; and optionally at least one excipient selected from the group consisting of gelling agents, antimicrobials, preservatives, and neutralizing agents.

2. The composition of claim 1, wherein the oxybutynin is present as oxybutynin free base, as a pharmaceutically acceptable salt of oxybutynin, or as a mixture thereof.

3. The composition of claim 2, wherein the pharmaceutically acceptable salt of oxybutynin is selected from the group consisting of acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate.

4. The composition of claim 1, wherein the alkanol is selected from the group consisting of ethanol, isopropanol, n-propanol, and mixtures thereof; wherein the polyalcohol is selected from the group consisting of propylene glycol, dipropylene glycol, and mixtures thereof; and
wherein the monoalkyl ether of diethylene glycol is selected from the group consisting of monomethyl ether of diethylene glycol, monoethyl ether of diethylene glycol, and mixtures thereof.

5. The composition of claim 1, wherein the at least one excipient selected from the group consisting of gelling agents, antimicrobials, preservatives, and neutralizing agents is present.

6. The composition of claim 1 wherein the formulation is in the form of a topical gel, lotion, foam, cream, spray, aerosol, ointment, emulsion, microemulsion, nanoemulsion, suspension, liposomal system, lacquer, patch, bandage, or occlusive dressing.

7. The composition according to claim 1 wherein the polyalcohol is present in an amount between about 20 to 30% by weight of the composition.

8. The composition according claim 1, wherein the oxybutynin is present as oxybutynin free base; and wherein the alkanol is selected from a group consisting of ethanol, isopropanol, and a mixture thereof in an amount between about 45 and 60% by weight of the composition; the polyalcohol is propylene glycol; the monoalkyl ether of diethylene glycol is monoethyl ether of diethylene glycol; and the polyalcohol and monoethyl ether of diethylene glycol are present in a weight ratio of 8:1.

9. A method for administering oxybutynin to a mammal in need thereof which comprises topically or transdermally administering to the skin or the mucosa of a mammal a composition according to claim 1.

10. The method of claim 9, wherein the mammal is a human and the oxybutynin is administered for treating hyperactivity of the detrusor muscle with frequent urge to urinate, increased urination during the night, urgent urination, involuntary urination with or without the urge to urinate, painful or difficult urination, detrusor hyperreflexia and detrusor instability.

11. The method of claim 10, wherein a daily dose of oxybutynin of between about 40 and about 100 mg is administered upon the abdomen, shoulder, arm, or thigh of the subject.

12. A composition for transdermal or transmucosal administration of oxybutynin consisting of:

oxybutynin present as oxybutynin free base, as a pharmaceutically acceptable salt of oxybutynin, or as a mixture thereof and in an amount between 1 to 3% by weight of the composition;
a delivery vehicle which consists of a C2 to C4 alkanol present in an amount of between about 45 to no more than 65% by weight of the composition, a polyalcohol selected from a group consisting of propylene glycol, dipropylene glycol, polyethylene glycol, glycerin, and mixtures thereof in an amount above 15 to 30% by weight of the composition, a monoalkyl ether of diethylene glycol in an amount between about 1 to 5% by weight of the composition, and water, to provide permeation enhancement of oxybutynin through mammalian dermal or mucosal surfaces; and
optionally at least one excipient selected from the group consisting of gelling agents, preservatives, and neutralizing agents.

13. The composition of claim 12, wherein the pharmaceutically acceptable salt of oxybutynin is selected from the group consisting of acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate.

14. The composition of claim 12, wherein the alkanol is selected from the group consisting of ethanol, isopropanol, n-propanol, and mixtures thereof; the polyalcohol is selected from the group consisting of propylene glycol, dipropylene glycol, polyethylene glycol, glycerin, and mixtures thereof and the monoalkyl ether of diethylene glycol is selected from the group consisting of monomethyl ether of diethylene glycol, monoethyl ether of diethylene glycol, and mixtures thereof.

15. The composition of claim 12, wherein the formulation is in the form of a topical gel.

16. The composition of claim 12, wherein the alkanol is present in an amount between about 45 and 60% by weight of the composition; the polyalcohol is present in an amount between about 20 to 30% by weight of the composition; the monoalkyl ether of diethylene glycol is monoethyl ether of diethylene glycol; and the polyalcohol and monoethyl ether of diethylene glycol are present in a weight ratio of 8:1.

17. A composition for transdermal or transmucosal administration of oxybutynin consisting of:

oxybutynin present as oxybutynin free base, as a pharmaceutically acceptable salt of oxybutynin, or as a mixture thereof and in an amount between 1 to 3% by weight of the composition;
a delivery vehicle which consists of ethanol present in an amount of between about 45 to no more than 60% by weight of the composition, a polyalcohol selected from a group consisting of propylene glycol and dipropylene glycol in an amount above 15 to about 20% by weight of the composition, monoethyl ether of diethylene glycol in an amount between about 1 to 5% by weight of the composition, and water, to provide permeation enhancement of oxybutynin through mammalian dermal or mucosal surfaces, with the polyalcohol and monoethyl ether of diethylene glycol present in a weight ratio of 8:1;
an excipient of a gelling agent so that the composition is in the form of a gel; and optionally at least one excipient selected from the group consisting of preservatives, and neutralizing agents.

18. The composition of claim 17, wherein the oxybutynin is present as oxybutynin free base in an amount of 3% by weight of the composition, the polyalcohol is propylene glycol in an amount of about 20% by weight of the composition, and the monoethyl ether of diethylene glycol is present in an amount of about 2.5% by weight of the composition.

19. The composition of claim 18, wherein gelling agent is present in an amount of 0.3% to 2%, and the neutralizing agent is hydrochloric acid.

20. The composition of claim 19, wherein the oxybutynin is present as the free base and in an amount of 3% by weight of the composition; and, the ethanol is anhydrous ethanol present in an amount of about 50.72% by weight of the composition, the polyalcohol is propylene glycol present in an amount of about 20% by weight of the composition, the monoethyl ether of diethylene glycol is present in an amount of about 2.5% by weight of the composition, the gelling agent is hydroxypropylcellulose in an amount of about 1 to 2% by weight of the composition, and the preservative is butylhydroxytoluene in an amount of about 0.05% by weight of the composition.

* * * * *

UNITED STATES PATENT AND TRADEMARK OFFICE
CERTIFICATE OF CORRECTION

PATENT NO. : 8,980,290 B2
APPLICATION NO. : 12/614216
DATED : March 17, 2015
INVENTOR(S) : Carrara et al.

It is certified that error appears in the above-identified patent and that said Letters Patent is hereby corrected as shown below:

Title Page:
Item (63) Related U.S. Application Data
Line 1, after "Continuation-in-part of application No.", insert -- 10/798,111, filed on Mar. 10, 2004, and is a continuation-in-part of application No. --; and
Lines 5-6, after "application No. PCT/EP2004/011175, filed on Oct. 6, 2004," delete "which is a continuation-in-part of application No. 10/798,111, filed on Mar. 10, 2004".

Item (63) the Related U.S. Application Data will correctly appear as follows:

-- Continuation-in-part of application No. 10/798,111, filed on Mar. 10, 2004, and is a continuation-in-part of application No. 11/755,923, filed on May 31, 2007, which is a continuation-in-part of application No. 11/371,042, filed on Mar. 7, 2006, now Pat. No. 7,335,379, which is a continuation of application No. PCT/EP2004/011175, filed on Oct. 6, 2004, said application No. 11/755,923 is a continuation-in-part of application No. 11/634,005, filed on Dec. 4, 2006, now Pat. No. 7,404,965, which is a continuation of application No. 10/343,570, filed as application No. PCT/EP01/09007 on Aug. 3, 2001, now Pat. No. 7,214,381. --.

In the Claims:
Column 23:
Line 43 (claim 8, line 3), after "alkanol is selected from", delete "a" and insert -- the --.

Column 24:
Line 8 (claim 12, line 10), after "selected from", delete "a" and insert -- the --.
Line 32 (claim 14, line 5), after ", and mixtures", delete "thereof" and insert -- thereof; --.
Line 55 (claim 17, line 10), before "group consisting of", delete "a" and insert -- the --.

Signed and Sealed this
Fourth Day of August, 2015

Michelle K. Lee
*Director of the United States Patent and Trademark Office*

CERTIFICATE OF CORRECTION (continued)
U.S. Pat. No. 8,980,290 B2

Column 25:
Line 7 (claim 19, line 1), before "gelling agent is", please insert -- the --.